(12) United States Patent
Barnett et al.

(10) Patent No.: US 6,342,583 B1
(45) Date of Patent: Jan. 29, 2002

(54) CDNAS CODING FOR MEMBERS OF THE CARCINOEMBRYONIC ANTIGEN FAMILY

(75) Inventors: Thomas R. Barnett, East Haven; James J. Elting, Madison; Michael E. Kamarck, Bethany, all of CT (US); Axel W. Kretschmer, Wulfrath (DE)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 08/027,974

(22) Filed: Mar. 8, 1993

Related U.S. Application Data

(60) Division of application No. 07/760,031, filed on Sep. 13, 1991, now Pat. No. 5,231,009, which is a division of application No. 07/274,107, filed on Nov. 21, 1988, now Pat. No. 5,122,599, which is a continuation-in-part of application No. 07/207,678, filed on Jun. 16, 1988, now abandoned, which is a continuation-in-part of application No. 07/060,031, filed on Jun. 19, 1987, now abandoned, which is a continuation-in-part of application No. 07/016,683, filed on Feb. 19, 1987, now abandoned, which is a continuation-in-part of application No. 06/896,361, filed on Aug. 13, 1986, now abandoned.

(51) Int. Cl.[7] ............................................... C07K 14/00
(52) U.S. Cl. ...................................................... 530/350
(58) Field of Search ......................................... 530/350

(56) References Cited

U.S. PATENT DOCUMENTS

| 4,228,236 A | 10/1980 | Jakstys et al. |
|---|---|---|
| 4,489,167 A | 12/1984 | Ochi et al. |

OTHER PUBLICATIONS

Gold, et al., J. Exp. Med., 121, 439–462 (1965).

*Primary Examiner*—Karen Cochrane Carlson
*Assistant Examiner*—Holly Schnizer
(74) *Attorney, Agent, or Firm*—Norris McLaughlin & Marcus

(57) ABSTRACT

A nucleic acid comprising a base sequence which codes for a CEA family member peptide sequence or nucleic acids having a base sequence hybridizable therewith, replicable recombinant cloning vehicles having an insert comprising such nucleic acid, cells transfected, infected or injected with such cloning vehicles, polypeptides expressed by such cells, synthetic peptides derived from the coding sequence of CEA family member nucleic acids, antibody preparations specific for such polypeptides, immunoassays for detecting CEA family members using such antibody preparations and nucleic acid hybridization methods for detecting CEA family member nucleic acid sequences using a nucleic acid probe comprising the above described nucleic acid.

2 Claims, 1 Drawing Sheet

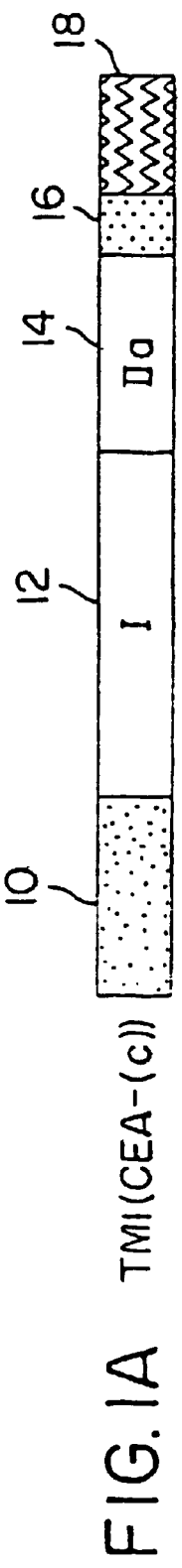
FIG.1A  TM1(CEA-(c))
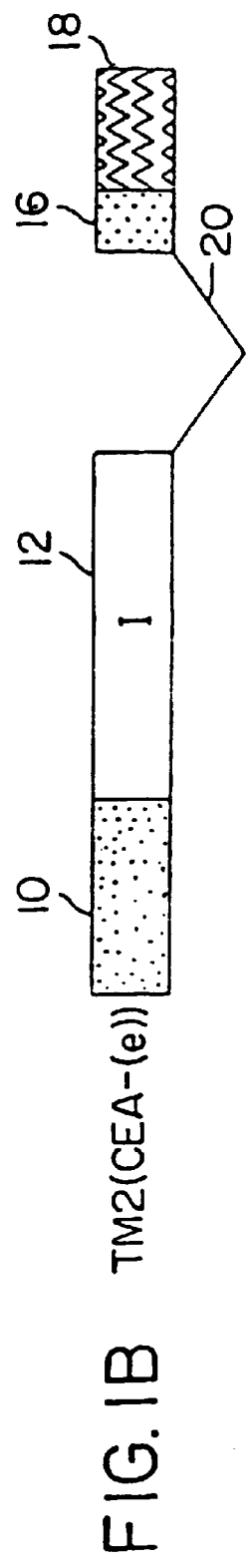
FIG.1B  TM2(CEA-(e))
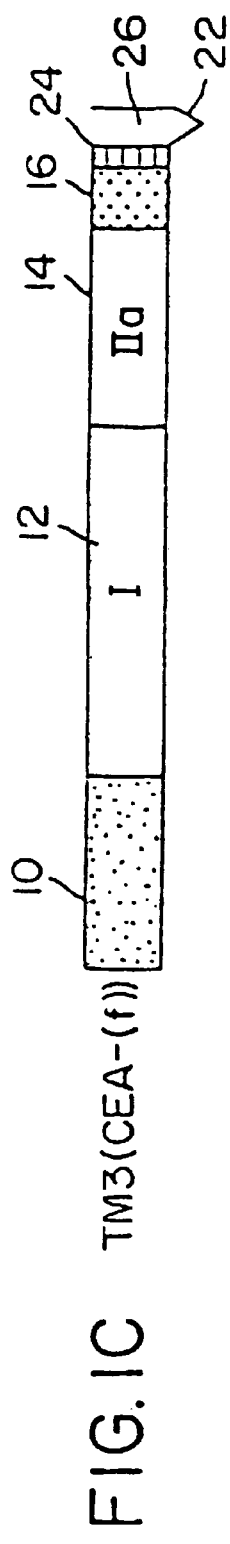
FIG.1C  TM3(CEA-(f))
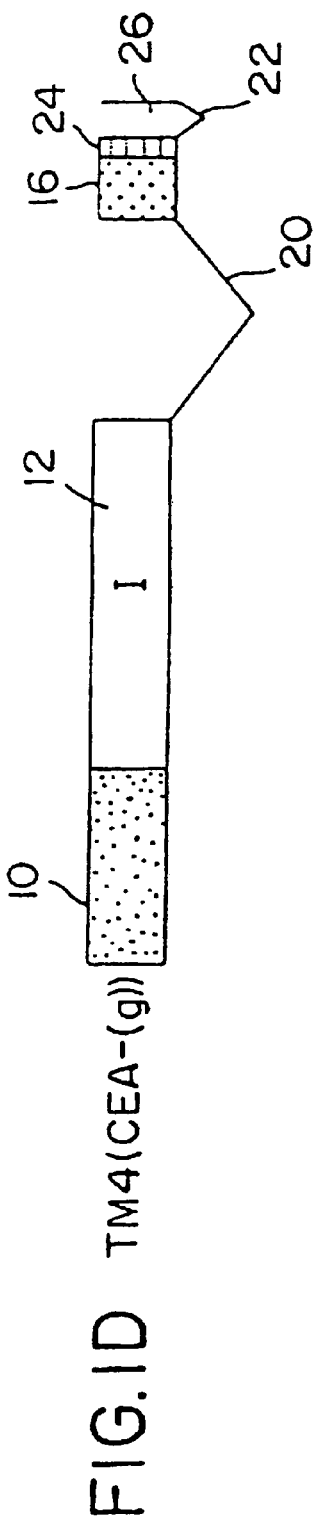
FIG.1D  TM4(CEA-(g))

CDNAS CODING FOR MEMBERS OF THE CARCINOEMBRYONIC ANTIGEN FAMILY

CROSS-REFERENCES TO RELATED APPLICATIONS

This is a division of application Ser. No. 07/760,031, filed Sep. 13, 1991, now U.S. Pat. No. 5,231,009, which is a division of Ser. No. 07/274,107 filed Nov. 21, 1988, now U.S. Pat. No. 5,122,599; which is a C-I-P of application Ser. No. 07/207,678 filed Jun. 16, 1988, now abandoned which is a C-I-P of application Ser. No. 07/060,031, filed Jun. 19, 1987, now abandoned, which is a C-I-P of application Ser. No. 07/016,683, filed Feb. 19, 1987, now abandoned, which is a C-I-P of application Ser. No. 06/896,361, filed Aug. 13, 1986, now abandoned.

BACKGROUND OF THE INVENTION

1. Field of the Invention

The present invention concerns nucleic acid sequences which code for carcinoembryonic antigen (CEA) antigen family peptide sequences.

2. Background Information

Carcinoembryonic antigen was first described by Gold and Freedman, *J. Exp. Med.,* 121, 439–462, (1965). CEA is characterized as a glycoprotein of approximately 200,000 molecular weight with 50–60% by weight of carbohydrate. CEA is present during normal human fetal development, but only in very low concentration in the normal adult intestinal tract. It is produced and secreted by a number of different tumors.

CEA is a clinically useful tumor marker for the management of colorectal cancer patients. CEA can be measured using sensitive immunoassay methods. When presurgical serum levels of CEA are elevated, a postsurgical drop in serum CEA to the normal range typically indicates successful resection of the tumor. Postsurgical CEA levels that do not return to normal often indicate incomplete resection of the tumor or the presence of additional tumor sites in the patient. After returning to normal levels, subsequent rapid rises in serum CEA levels usually indicate the presence of metastages. Slower postsurgical rises from the normal level are most often interpreted to indicate the presence of new primary tumors not previously detected. Post surgical management of colon cancer patients is thus facilitated by the measurement of CEA.

CEA is a member of an antigen family. Because of this, the immunoassay of CEA by presently available methods is complicated by the fact that CEA is but one of several potentially reactive antigens. There have been at least sixteen CEA-like antigens described in the literature. Since some of these appear to be the same antigen described by different investigators, the actual number of different antigens is somewhat less than this number. Nonetheless, there is a complex array of cross-reactive antigens which can potentially interfere with an immunoassay of the CEA released by tumors. It is known that serum levels of CEA-like antigens are elevated in many non-cancerous conditions such an inflammatory liver diseases and also in smokers. It is important that immunoassays used for the monitoring of cancer patient status not be interfered with by these other CEA-like antigens. Conversely, it is important to be able to distinguish the antigens by immunoassays because of the possibility that different tumor types may preferentially express different forms of CEA. If so, then the ability to reliably measure the different forms of CEA can provide the means to diagnose or more successfully treat different forms of cancer.

The members of the "CEA family" share some antigenic determinants. These common epitopes are not useful in distinguishing the members of the antigen family and antibodies recognizing them are of little use for measuring tumor-specific CEA levels.

U.S. Pat. No. 3,663,684, entitled "Carcinoembryonic Antigen and Diagnostic Method Using Radioactive Iodine", concerns purification and radioiodination of CEA for use in a RIA.

U.S. Pat. No. 3,697,638 describes that CEA is a mixture of antigens (components A and B in this case). U.S. Pat. No. 3,697,638 mentions methods for separating and radioiodinating each component and their use in specific RIA's.

U.S. Pat. No. 3,852,415, entitled "Compositions for Use in Radioimmunoassay, as Substitute for Blood Plasma Extract in Determination of Carcinoembryonic Antigen" relates to the use of a buffer containing EDTA and bovine serum albumin as a substitute for plasma as a diluent for CEA RIA's.

U.S. Pat. No. 3,867,363, entitled "Carcinoembryonic Antigens", is directed to the isolation of CEA components A and B, their labelling and use in a RIA.

U.S. Pat. No. 3,927,193, entitled "Localization of Tumors by Radiolabelled Antibodies", concerns the use of radiolabelled anti-CEA antibodies in whole body tumor imaging.

U.S. Pat. No. 3,956,258, entitled "Carcinoembryonic Antigens", relates to the isolation of CEA components A and B.

U.S. Pat. No. 4,086,217, entitled "Carcinoembryonic Antigens", is directed to the isolation of CEA components A and B.

U.S. Pat. No. 4,140,753, entitled "Diagnostic Method and Reagent", concerns the purification of a CEA isomer called CEA-S1 and its use in a RIA.

U.S. Pat. No. 4,145,336, entitled "Carcinoembryonic Antigen Isomer", relates to the antigen CEA-S1.

U.S. Pat. No. 4,180,499, entitled "Carcinoembryonic Antigens", describes a process for producing CEA component B.

U.S. Pat. No. 4,228,236, entitled "Process of Producing Carcinoembryonic Antigen", is directed to the use of the established cell lines LS-174T and LS-180 or clones or derivatives thereof for the production of CEA.

U.S. Pat. No. 4,272,504, entitled "Antibody Adsorbed Support Method for Carcinoembryonic Antigen Assay", concerns two concepts for the radioimmunoassay of CEA. First, U.S. Pat. No. 4,272,504 relates to a sample pretreatment in the form of heating to 65 to 85° C. at pH 5 to precipitate and eliminate extraneous protein. Second, it describes the use of a solid phase antibody (either on beads or tubes) as a means to capture analyte and radiolabelled CEA tracer.

U.S. Pat. No. 4,299,815, entitled "Carcinoembryonic Antigen Determination", concerns diluting a CEA sample with water and pretreating by heating to a temperature below which precipitation of protein will occur. The pretreated sample is then immunoassayed using RIA, EIA, FIA or chemiluminescent immunoassay.

U.S. Pat. No. 4,349,528, entitled "Monoclonal Hybridoma Antibody Specific for High Molecular Weight Carcinoembryonic Antigen", is directed to a monoclonal antibody reacting with 180 kD CEA, but not with other molecular weight forms.

U.S. Pat. No. 4,467,031, entitled "Enzyme-Immunoassay for Carcinoembryonic Antigen", relates to a sandwich enzyme immunoassay for CEA in which the first of two anti-CEA monoclonal antibodies is attached to a solid phase and the second monoclonal is conjugated with peroxidase.

U.S. Pat. No. 4,489,167, entitled "Methods and Compositions for Cancer Detection", describes that CEA shares an antigenic determinant with alpha-acid glycoprotein (AG), which is a normal component of human serum. The method described therein concerns a solid-phase sandwich enzyme immunoassay using as one antibody an antibody recognizing AG and another antibody recognizing CEA, but not AG.

U.S. Pat. No. 4,578,349, entitled "Immunoassay for Carcinoembryonic Antigen (CEA)", is directed to the use of high salt containing buffers as diluents in CEA immunoassays.

EP 113072-A, entitled "Assaying Blood Sample for Carcinoembryonic Antigen—After Removal of Interfering Materials by Incubation with Silica Gel", relates to the removal from a serum of a plasma sample of interfering substances by pretreatment with silica gel. The precleared sample is then subjected to an immunoassay.

EP 102008-A, entitled "Cancer Diagnostics Carcinoembryonic Antigen—Produced from Perchloric Acid Extracts Without Electrophoresis", relates to a procedure for the preparation of CEA from perchloric acid extracts, without the use of an electrophoresis step.

EP 92223-A, entitled "Determination of Carcinoembryonic Antigen in Cytosol or Tissue—for Therapy Control and Early Recognition of Regression", concerns an immunoassay of CEA, not in serum or plasma, but in the cytosol fraction of the tumor tissue itself.

EP 83103759.6, entitled "Cytosole-CEA-Measurement as Predictive Test in Carcinoma, Particularly Mammacarcinoma", is similar to EP 92223-A.

EP 83303759, entitled "Monoclonal Antibodies Specific to Carcinoembryonic Antigen", relates to the production of "CEA specific" monoclonal antibodies and their use in immunoassays.

WO 84/02983, entitled "Specific CEA-Family Antigens, Antibodies Specific Thereto and Their Methods of Use", is directed to the use of monoclonal antibodies to CEA-meconium (MA)-, and NCA-specific epitopes in immunoassays designed to selectively measure each of these individual components in a sample.

All of the heretofore CEA assays utilize either monoclonal or polyclonal antibodies which are generated by immunizing animals with the intact antigen of choice. None of them address the idea of making sequence specific antibodies for the detection of a unique primary sequence of the various antigens. They do not cover the use of any primary amino acid sequence for the production of antibodies to synthetic peptides or fragments of the natural product. They do not include the concept of using primary amino acid sequences to distinguish the CEA family members. None of them covers the use of DNA or RNA clones for isolating the genes with which to determine the primary sequence.

DEFINITIONS

Nucleic Acid Abbreviations

| | |
|---|---|
| A | adenine |
| G | guanine |
| C | cytosine |
| T | thymidine |
| U | uracil |

-continued
DEFINITIONS

Amino Acid Abbreviations:

| | |
|---|---|
| Asp | aspartic acid |
| Asn | asparagine |
| Thr | threonine |
| Ser | serine |
| Glu | glutamic acid |
| Gln | glutamine |
| Pro | proline |
| Gly | glycine |
| Ala | alanine |
| Cys | cysteine |
| Val | valine |
| Met | methionine |
| Ile | isoleucine |
| Leu | leucine |
| Tyr | tyrosine |
| Phe | phenylalanine |
| Trp | tryptophan |
| Lys | lysine |
| His | histidine |
| Arg | arginine |

Nucleotide—A monomeric unit of DNA or RNA containing a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses.

Functional equivalents—It is well known in the art that in a DNA sequence some nucleotides can be replaced without having an influence on the sequence of the expression product. With respect to the peptide this term means that one or more amino acids which have no function in a particular use can be deleted or replaced by another one.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode the amino acid leucine ("Leu"), TAG, TAA and TGA are translation stop signals and ATG is a translation start signal.

Reading Frame—The grouping of codons during translation of mRNA into amino acid sequences. During translation, the proper reading frame must be maintained. For example, the sequence GCTGGTTGTAAG may be translated in three reading frames or phases, each of which affords a different amino acid sequence GCT GGT TGT AAG—Ala-Gly-Cys-Lys G CTG GTT GTA AG—Leu-Val-Val GC TGG TTG TAA G—Trp-Leu-(STOP).

Polypeptide—A linear array of amino acids connected one to the other by peptide bonds between the alpha-amino and carboxy groups of adjacent amino acids.

Genome—The entire DNA of a cell or a virus. It includes inter alia the structural genes coding for the polypeptides of the cell or virus, as well as its operator, promoter and ribosome binding and interaction sequences, including sequences such as the Shine-Delgarno sequences.

Structural Gene—A DNA sequence which encodes through its template or messenger RNA ("mRNA") a sequence of amino acids characteristics of a specific polypeptide.

Transcription—The process of producing mRNA from a structural gene.

Translation—The process of producing a polypeptide from mRNA.

Expression—The process undergone by a structural gene to produce a polypeptide. It is a combination of transcription and translation.

Plasmid—A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (Tet$^R$) transforms a cell previously sensitive to tetracycline into one which is resistant to it. A cell transformed by a plasmid is called a "transformant".

Phage or Bacteriophage—Bacterial virus, many of which consist of DNA sequences encapsulated in a protein envelope or coat ("capsid protein").

Cloning Vehicle—A plasmid, phage DNA or other DNA sequence which is capable of replicating in a host cell, which is characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and have the capacity to infect some host cell and be maintained therein.

cDNA Expression Vector—A procaroytic cloning vehicle which also contains sequences of nucleotides that facilitate expression of cDNA sequences in eucaroytic cells. These nucleotides include sequences that function as eucaryotic promoter, alternative splice sites and polyadenylation signals.

Transformation/Transfection—DNA or RNA is introduced into cells in such a way as to allow gene expression. "Infected" referred to herein concerns the introduction of RNA or DNA by a viral vector into the host.

"Injected" referred to herein concerns the microinjection (use of a small syringe) of DNA into a cell.

CEA antigen family (CEA gene family)—a set of genes (gene family) and their products (antigen family) that share nucleotide sequences homologous to partial cDNA LV-7 (CEA -(a)) and as a result of theses similarities also share a subset of their antigenic epitopes. Examples of the CEA antigen family include CEA (=CEA-(b)), transmembrane CEA (TMCEA)=(CEA-(c) and normal crossrecting antigen NCA (=CEA-(d)).

SUMMARY OF THE INVENTION

The present invention concerns the following DNA sequences designed as TM-2 (CEA-(e)), TM-3 (CEA-(f)), TM-4 (CEA-(g)), KGCEA1 and KGCEA2, which code for CEA antigen family peptide sequences or nucleic acids having a base sequence (DNA or RNA) that are hybridizable therewith:

| SEQUENCE AND TRANSLATION OF CDNA OF TM-2 |
|---|
| 10　　　　　　　　　　　30　　　　　　　　　　　50 |
| CAGCCGTGCTCGAAGCGTTCCTGGAGCCCAAGCTCTCCTCCACAGGTGAAGACAGGGCCA |
| 70　　　　　　　　　　　90　　　　　　　　　　　110 |
| GCAGGAGACACCATGGGGCACCTCTCAGCCCCACTTCACAGAGTGCGTGTACCCTGGCAG<br>　　　　　　　　　　MetGlyHiSLeuSerAlaProLeuHisArgValArgValProTrpGln |
| 130　　　　　　　　　　150　　　　　　　　　　170 |
| GGGCTTCTGCTCACAGCCTCACTTCTAACCTTCTGGAACCCGCCCACCACTGCCCAGCTC<br>GlyLeuLeuLeuThrAlaSerLeuLeuThrPheTrpAsnProProThrThrAlaGlnLeu |
| 190　　　　　　　　　　210　　　　　　　　　　230 |
| ACTACTGAATCCATGCCATTCAATGTTGCAGAGGGGAAGGAGGTTCTrCTCCTTGTCCAC<br>ThrThrGluSerMetProPheAsnValAlaGlyGlyLysGluValLeuLeuLeuValHis |
| 250　　　　　　　　　　270　　　　　　　　　　290 |
| AATCTGCCCCAGCAACTTTTTGGCTACAGCTGGTACAAAGGGGAAAGAGTGGATGGCAAC<br>AsnLeuProGlnGlyLeuPheGlyTyrSerTrpTysLysGlyGluArgValAspGlyAsn |
| 310　　　　　　　　　　330　　　　　　　　　　350 |
| CGTCAAATTGTAGGATATGCAATAGGAACTCAACAAGCTACCCCAGGGCCCGCAAACAGC<br>ArgGlnIleValGlyTyrAlaIleGlyThrGlnGlnAlaThrProGlyProAlaAsnSer |
| 370　　　　　　　　　　390　　　　　　　　　　410 |
| GGTCGAGAGACAATATACCCCAATGCATCCCTGCTGATCCAGAACGTCACCCAGAATGAC<br>GlyArgGluThrIleTyrProAsnAlaSerLeuLeuIleGlnAsnValThrGlnAsnAsp |

-continued
SEQUENCE AND TRANSLATION OF CDNA OF TM-2

```
         430              450              470
          .                .                .
ACAGGATTCTACACCCTACAAGTCATAAAGTCAGATCTTGTGAATGAAGAAGCAACTGGA
ThrGlyPheTyrThrLeuGlnValIleLysSerAspLeuValAsnGluGluAlaThrGly 490              510              530
          .                .                .
CAGTTCCATGTATACCCGGAGCTGCCCAAGCCCTCCATCTCCAGCAACAACTCCAACCCT
GlnPheHisValTyrProGluLeuProLysProSerIleSerSerAsnAsnSerAsnPro 550              570              590
          .                .                .
GTGGAGGACAAGGATGCTGTGGCCTTCACCTGTGAACCTGAGACTCAGGACACAACCTAC
ValGluAspLysAspAlaValAlaPheThrCysGluProGluThrGlnAspThrThrTyr 610              630              650
          .                .                .
CTGTGGTGGATAAACAATCAGAGCCTCCCGGTCAGTCCCAGGCTGCAGCTGTCCAATGGC
LeuTrpTrpIleAsnAsnGlnSerLeuProValSerProArgLeuGlnLeuSerAsnGly 670              690              710
          .                .                .
AACAGGACCCTCACTCTACTCAGTGTCACAAGGAATGACACAGGACCCTATGAGTGTGAA
AsnArgThrLeuThrLeuLeuSerValThrArgAsnAspThrGlyProTyrGluCysGlu 730              750              770
          .                .                .
ATACAGAACCCAGTGAGTGCGAACCGCAGTGACCCAGTCACCTTGAATGTCACCTATGGC
IleGlnAsnProValSerAlaAsnArgSerAspProValThrLeuAsnValThrTyrGly 790              810              830
          .                .                .
CCGGACACCCCCACCATTTCCCCTTCAGACACCTATTACCGTCCAGGGGCAAACCTCAGC
ProAspThrProThrIleSerProSerAspThrTyrTyrArgProGlyAlaAsnLeuSer 850              870              890
          .                .                .
CTCTCCTGCTATGCAGCCTCTAACCCACCTGCACAGTACTCCTGGCTTATCAATGGAACA
LeuSerCysTyrAlaAlaSerAsnProProAlaGlnTyrSerTrpLeuIleAsnGlyThr 910              930              950
          .                .                .
TTCCAGCAAAGCACACAAGAGCTCTTTATCCCTAACATCACTGTGAATAATAGTGGATCC
PheGlnGlnSerThrGlnGluLeuPheIleProAsnIleThrValAsnAsnSerGlySer 970              990             1010
          .                .                .
TATACCTGGACGCCAATAACTCAGTCACTTGGCTGCAACAGGACCACAGTCAAGACGATC
TyrThrCysHisAlaAsnAsnSerValThrGlyCysAsnArgThrThrValLysThrIle 1030             1050             1070
          .                .                .
ATAGTCACTGATAATGCTCTACCACAAGAAAATGGCCTCTCACCTGGGGCCATTGCTGGC
IleValThrAspAsnAlaLeuProGlnGluAsnGlyLeuSerProGlyAlaIleAlaGly 1090             1110             1130
          .                .                .
ATTGTGATTGGAGTAGTGGCCCTGGTTGCTCTGATAGCAGTAGCCCTGGCATGTTTTCTG
IleValIleGlyValValAlaLeuValAlaLeuIleAlaValAlaLeuAlaCysPheLeu 1150             1170             1190
          .                .                .
CATTTCGGGAAGACCGGCAGGGCAAGCGACCAGCGTGATCTCACAGAGCACAAACCCTCA
HisPheGlyLysThrGlyArgAlaSerAspGlnArgAspLeuThrGluHisLysProSer 1210             1230             1250
          .                .                .
GTCTCCAACCACACTCAGGACCACTCCAATGACCCACCTAACAAGATGAATGAAGTTACT
ValSerAsnHisThrGlnAspHisSerAsnAspProProAsnLysMetAsnGluValThr 1270             1290             1310
          .                .                .
TATTCTACCCTGAACTTTGAAGCCCAGCAACCCACACAACCAACTTCAGCCTCCCCATCC
TyrSerThrLeuAsnPheGluAlaGlnGlnProThrGlnProThrSerAlaSerProSer 1330             1350             1370
```

SEQUENCE AND TRANSLATION OF CDNA OF TM-2

-continued

CTAACAGCCACAGAAATAATTTATTCAGAAGTAAAAAAGCAGTAATGAAACCTGTCCTGC
LeuThrAlaThrGluIleIleTyrSerGluValLysLysGln 1390     1410     1430

TCACTGCAGTGCTGATGTATTTCAAGTCTCTCACCCTCATCACTAGGAGATTCCTTTCCC 1450     1470     1490

CTGTAGGGTAGAGGGTGGGGACAGAAACAACTTTCTCCTACTCTTCCTTCCTAATAGGC 1510     1530     1550

ATCTCCAGGCTGCCTGGTCACTGCCCCTCTCAGTGTCAATAGATGAAAGTACATTGGG 1570     1590     1610

AGTCTGTAGGAAACCCAACCTTCTTGTCATTGAAATTTGGCAAAGCTGACTTTGGGAAAG 1630     1650     1670

AGGGACCAGAACTTCCCCTCCCTTCCCCTTTTCCCAACCTGGACTTGTTTTAAACTTGCC 1690     1710     1730

TGTTCAGAGCACTCATTCCTTCCCACCCCCAGTCCTGTCCTATCACTCTAATTCGGATTT 1750     1770     1790

GCCATAGCCTTGAGGTTATGTCCTTTTCCATTAAGTACATGTGCCAGGAAACAGCGAGAG 1810     1830     1850

AGAGAAAGTAAACGGCAGTAATGCTTCTCCTATTTCTCCAAAGCCTTGTGTGAACTAGCA 1870     1890     1910

AAGAGAAGAAAATCAAATATATAACCAATAGTGAAATGCCACAGGTTTGTCCACTGTCAG 1930     1950     1970

GGTTGTCTACCTGTAGGATCAGGGTCTAAGCACCTTGGTGCTTAGCTAGAATACCACCTA 1990     2010     2030

ATCCTTCTGGCAAGCCTGTCTTCAGAGAACCCACTAGAAGCAACTAGGAAAAATCACTTG 2050     2070     2090

CCAAAATCCAAGGCAATTCCTGATGGAAAATGCAAAAGCACATATATGTTTTAATATCTT 2110     2130     2150

TATGGGCTCTGTTCAAGGCAGTGACTGAGAGGGAGGGGTTATAGCTCAGGAGGGAACCAG 2170     2190     2210

CTTCTGATAAACACAATCTGCTAGGAACTTGGGAAAGGAATCAGAGAGCTGCCCTTCAGC 2230     2250     2270

GATTATTTAAATTGTTAAAGAATACACAATTTGGGGTATTGGGATTTTTCTCCTTTTCTC 2290     2310     2330

TGAGACATTCCACCATTTTAATTTTTGTAACTGCTTATTTATGTGIAAAGGGTTATTTTT 2350     2370     2390

ACTTAGCTTAGCTATGTCAGCCAATCCGATTGCCTTAGGTGAAAGAAACCACCGAAATCC 2410     2430     2450

CTCAGGTCCCTTGGTCAGGAGCCTCTCAAGATTTTTTTTGTCAGAGGCTCCAAATAGAAA 2470     2490     2510

| SEQUENCE AND TRANSLATION OF CDNA OF TM-2 |
| --- |

```
                   2530              2550              2570
                     .                 .                 .
ATAAGAAAAGGTTTTCTTCATTCATGGCTAGAGCTAGATTTAACTCAGTTTCTAGGCACC 2590              2610              2630
                     .                 .                 .
TCAGACCAATCATCAACTACCATTCTATTCCATGTTTGCACCTGTGCATTTTCTGTTTGC 2650              2670              2690
                     .                 .                 .
CCCCATTCACTTTGTCAGGAAACCTTGGCCTCTGCTAAGGTGTATTTGGTCCTTGAGAAG 2710              2730              2750
                     .                 .                 .
TGGGAGCACCCTACAGGGACACTATCACTCATGCTGGTGGCATTGTTTACAGCTAGAAAG 2770              2790              2810
                     .                 .                 .
CTGCACTGGTGCTAATGCCCCTTGGGAAATGGGGCTGTGAGGAGGAGGATTATAACTTAG 2830              2850              2870
                     .                 .                 .
GCCTAGCCTCTTTTAACAGCCTCTGAAATTTATCTTTTCTTCTATGGGGTCTATAAATGT 2890              2910              2930
                     .                 .                 .
ATCTTATAATAAAAAGGAAGGACAGGAGGAAGACAGGCAAATGTACTTCTCACCCAGTCT 2950              2970              2990
                     .                 .                 .
TCTACACAGATGGAATCTCTTTGGGGCTAAGAGAAAGGTTTTATTCTATATTGCTTACCT 3010              3030              3050
                     .                 .                 .
GATCTCATGTTAGGCCTAAGAGGCTTTCTCCAGGAGGATTAGCTTGGAGTTCTCTATACT 3070              3090              3110
                     .                 .                 .
CAGGTACCTCTTTCAGGGTTTTCTAACCCTGACACGGACTGTGCATACTTTCCCTCATCC 3130              3150              3170
                     .                 .                 .
ATGCTGTGCTGTGTTATTTAATTTTTCCTGGCTAAGATCATGTCTGAATTATGTATGAAA

ATTATTCTATGTTTTTATAATAAAAATAATATATCAGACATCGAAAAAAAAAA
```

| SEQUENCE AND TRANSLATION OF cDNA OF TM-3 |
| --- |

```
                    10                30                50
                     .                 .                 .
CAGCCGTGCTCGAAGCGTTCCTGGAGCCCAAGCTCTCCTCCACAGGTGAAGACAGGGCCA 70                90               110
                     .                 .                 .
GCAGGAGACACCATGGGGCACCTCTCAGCCCCACTTCACAGAGTGCGTGTACCCTGGCAG
          MetGlyHisLeuSerAlaProLeuHisArgValArgValProTrpGln 130               150               170
                     .                 .                 .
GGGCTTCTGCTCACAGCCTCACTTCTAACCTTCTGGAACCCGCCCACCACTGCCCAGCTC
GlyLeuLeuLeuThrAlaSerLeuLeuThrPheTrpAsnProProThrThrAlaGlnLeu 190               210               230
                     .                 .                 .
ACTACTGAATCCATGCCATTCAATGTTGCAGAGGGGAAGGAGGTTCTTCTCCTTGTCCAC
ThrThrGluSerIleProPheAsnValAlaGluGlyLysGluValLeuLeuLeuValHis 250               270               290
                     .                 .                 .
AATCTGCCCCAGCAACTTTTTGGCTACAGCTGGTACAAAGGGGAAAGAGTGGATGGCAAC
AsnLeuProGlnGlnLeuPheGlyTyrSerTrpTyrLysGlyGluArgValAspGlyAsn
```

-continued

SEQUENCE AND TRANSLATION OF cDNA OF TM-3

```
       310                 330                 350
         .                   .                   .
CGTCAAATTGTAGGATATGCAATAGGAACTCAACAAGCTACCCCAGGGCCCGCAAACAGC
ArgGlnIleValGlyTyrAlaIleGlyThrGlnGlnAlaThrProGlyProAlaAsnSer 370                 390                 410
         .                   .                   .
GGTCGAGAGACAATATACCCCAATGCATCCCTGCTGATCCAGAACGTCACCCAGAATGAC
GlyArgGluThrIleTyrProAsnAlaSerLeuLeuIleGlnAsnValThrGlnAsnAsp 430                 450                 470
         .                   .                   .
ACAGGATTCTACACCCTACAAGTCATAAAGTCAGATCTTGTGAATGAAGAAGCAACTGGA
ThrGlyPheTyrThrLeuGlnValIleLysSerAspLeuValAsnGluGluAlaThrGly 490                 510                 530
         .                   .                   .
CAGTTCCATGTATACCCGGAGCTGCCCAAGCCCTCCATCTCCAGCAACAACTCCAACCCT
GlnPheHisValTyrProGluLeuProLysProSerIleSerSerAsnAsnSerAsnPro 550                 570                 590
         .                   .                   .
GTGGAGGACAAGGATGCTGTGGCCTTCACCTGTGAACCTGAGACTCAGGACACAACCTAC
ValGluAspLysAspAlaValAlaPheThrCysGluProGluThrGlnAspThrThrTyr 610                 630                 650
         .                   .                   .
CTGTGGTGGATAAACAATCAGAGCCTCCCGGTCAGTCCCAGGCTGCAGCTGTCCAATGGC
LeuTrpTrpIleAsnAsnGlnSerLeuProValSerProArgLeuGlnLeuSerAsnGly 670                 690                 710
         .                   .                   .
AACAGGACCCTCACTCTACTCAGTGTCACAAGGAATGACACAGGACCCTATGAGTGTGAA
AsnArgThrLeuThrLeuLeuSerValThrArgAsnAspThrGlyProTyrGluCysGlu 730                 750                 770
         .                   .                   .
ATACAGAACCCAGTGAGTGCGAACCGCAGTGACCCAGTCACCTTGAATGTCACCTATGGC
IleGlnAsnProValSerAlaAsnArgSerAspProValThrLeuAsnValThrTyrGly 790                 810                 830
         .                   .                   .
CCGGACACCCCCACCATTTCCCCTTCAGACACCTATTACCGTCCAGGGGCAAACCTCAGC
ProAspThrProThrIleSerProSerAspThrTyrTyrArgProGlyAlaAsnLeuSer 850                 870                 890
         .                   .                   .
CTCTCCTGCTATGCAGCCTCTAACCCACCTGCACAGTACTCCTGGCTTATCAATGGAACA
LeuSerCysTyrAlaAlaSerAsnProProAlaGlnTyrSerTrpLeuIleAsnGlyThr 910                 930                 950
         .                   .                   .
TTCCAGCAAAGCACACAAGAGCTCTTTATCCCTAACATCACTGTGAATAATAGTGGATCC
PheGlnGlnSerThrGlnGluLeuPheIleProAsnIleThrValAsnAsnSerGlySer 970                 990                1010
         .                   .                   .
TATACCTGCCACGCCAATAACTCAGTCACTGGCTGCAACAGGACCACAGTCAAGACGATC
TyrThrCysHisAlaAsnAsnSerValThrGlyCysAsnArgThrThrValLysThrIle 1030                1050                1070
         .                   .                   .
ATAGTCACTGAGCTAAGTCCAGTAGTAGCAAAGCCCCAAATCAAAGCCAGCAAGACCACA
IleValThrGluLeuSerProValAlaLysProGlnIleLysLysAlaSerLysThrThr 1090                1110                1130
         .                   .                   .
GTCACAGGAGATAAGGACTCTGTGAACCTGACCTGCTCCACAAATGACACTGGAATCTCC
ValThrGlyAspLysAspSerValAsnLeuThrCysSerThrAsnAspThrGlyIleSer 1150                1170                1190
         .                   .                   .
ATCCGTTGGTTCTTCAAAAACCAGAGTCTCCCGTCCTCGGAGAGGATGAAGCTGTCCCAG
IleArgTrpPhePheLysAsnGlnSerLeuProSerSerGluArgMetLysLeuSerGln 1210                1230                1250
```

| SEQUENCE AND TRANSLATION OF cDNA OF TM-3 |
|---|

```
GGCAACACCACCCTCAGCATAAACCCTGTCAAGAGGGAGGATGCTGGGACGTATTGGTGT
GlyAsnThrThrLeuSerIleAsnProValLysArgGluAspAlaMetLysLeuSerGln 1270          1290          1310
          .             .             .
GAGGTCTTCAACCCAATCAGTAAGAACCAAAGCGACCCCATCATGCTGAACGTAAACTAT
GluValPheAsnProIleSerLysAsnGlnSerAspProIleMetLeuAsnValAsnTyr 1330          1350          1370
          .             .             .
AATGCTCTACCACAAGAAAATGGCCTCTCACCTGGGGCCATTGCTGGCATTGTGATTGGA
AsnAlaLeuProGlnGlnAsnGlyLeuSerProGlyAlaIleAlaGlyIleValIleGly 1390          1410          1430
          .             .             .
GTAGTGGCCCTGGTTGCTCTGATAGCAGTAGCCCTGGCATGTTTTCTGCATTTCGGGAAG
ValValAlaLeuValAlaLeuIleAlaValAlaLeuAlaCysPheLeuHisPheGlyLys 1450          1470          1490
          .             .             .
ACCGGCAGCTCAGGACCACTCCAATGACCCCACCTAACAAGATGAATGAAGTTACTTATTC
ThrGlySerSerGlyProLeuGln 1510          1530          1550
          .             .             .
TACCCTGAACTTTGAAGCCCAGCAACCCACACAACCAACTTCAGCCTCCCCATCCCTAAC 1570          1590          1610
          .             .             .
AGCCACAGAAATAATTTATTCAGAAGTAAAAAAGCAGTAATGAAACCTGAAAAAAAAAAA

1630
          .
AAAAAAAAAA
```

| SEQUENCE AND TRANSLATION OF CDNA OF TM-4 |
|---|

```
         10            30            50
          .             .             .
CAGCCGTGCTCGAAGCGTTCCTGGAGCCCAAGCTCTCCTCCACAGGTGAAGACAGGGCCA 70            90           110
          .             .             .
GCAGGAGACACCATGGGGCACCTCTCAGCCCCACTTCACAGAGTGCGTGTACCCTGGCAG
          MetGlyHisLeuSerAlaProLeuHisArgValArgValProTrpGln 130           150           170
          .             .             .
GGGCTTCTGCTCACAGCCTCACTTCTAACCTTCTGGAACCCGCCCACCACTGCCCAGCTC
GlyLeuLeuLeuThrAlaSerLeuLeuThrPheTrpAsnProProThrThrAlaGlnLeu 190           210           230
          .             .             .
ACTACTGAATCCATGCCATTCAATGTTGCAGAGGGGAAGGAGGTTCTTCTCCTTGTCCAC
ThrThrGluSerMetProPheAsnValAlaGluGlyLysGlyValLeuLeuLeuValHis 250           270           290
          .             .             .
AATCTGCCCCAGCAACTTTTTGGCTACAGCTGGTACAAGGGGIkAAGAGTGGATGGCAAC
AsnLeuProGlnGlnLeuPheGlyTyrSerTrpTyrLysGlyGlyArgValAspGlyAsn 310           330           350
          .             .             .
CGTCAAATTGTAGGATATGCAATAGGAACTCAACAAGCTACCCCAGGGCCCGCAAACAGC
ArgGlnIleValGlyTyrAlaIleGlyThrGlnGlnAlaThrProGlyProAlaAsnSer 370           390           410
          .             .             .
GGTCGAGAGACAATATACCCCAATGCATCCCTGCTGATCCAGAACGTCACCCAGAATGAC
GlyArgGluThrIleTyrProAsnAlaSerLeuLeuIleGlnAsnValThrGlnAsnAsp
```

-continued

| SEQUENCE AND TRANSLATION OF CDNA OF TM-4 |
|---|

```
         430              450              470
          .                .                .
ACAGGATTCTACACCCTACAAGTCATAAAGTCAGATCTTGTGAATGAAGAAGCAACTGGA
ThrGlyPheTyrThrLeuGlnValIleLysSerASpLeuValAsnGluGluAlaThrGly 490              510              530
          .                .                .
CAGTTCCATGTATACCCGGAGCTGCCCAAGCCCTCCATCTCCAGCAACAACTCCAACCCT
GlnPheHisValTyrProGluLeuProLysProSerIleSerSerAsnAsnSerAsnPro 550              570              590
          .                .                .
GTGGAGGACAAGGATGCTGTGGCCTTCACCTGTGAACCTGAGACTCAGGACACAACCTAC
ValGluAspLysAspAlaValAlaPheThrCysGluProGluThrGlnAspThrThrTyr 610              630              650
          .                .                .
CTGTGGTGGATAAACAATCAGAGCCTCCCGGTCAGTCCCAGGCTGCAGCTGTCCAATGGC
LeuTrpTrpIleAsnAsnGlnSerLeuProValSerProArgLeuGlnLeuSerAsnGly 670              690              710
          .                .                .
AACAGGACCCTCACTCTACTCAGTGTCACAAGGAATGACACAGGACCCTATGAGTGTGAA
AsnArgThrLeuThrLeuLeuSerValThrArgAsnAspThrGlyProTyrGluCysGlu 730              750              770
          .                .                .
ATACAGAACCCAGTGAGTGCGAACCGCAGTGACCCAGTCACCTTGAATGTCACCTATGGC
IleGlnAsnProValSerAlaAsnArgSerAspProValThrLeuAsnValThrTyrGly 790              810              830
          .                .                .
CCGGACACCCCCACCATTTCCCCTTCAGACACCTATTACCGTCCAGGGGCAAACCTCAGC
ProAspThrProThrIleSerProSerAspThrTyrTyrArgProGlyAlaAsnLeuSer 850              870              890
          .                .                .
CTCTCCTGCTATGCAGCCTCTAACCCACCTGCACAGTACTCCTGGCTTATCAATGGAACA
LeuSerCysTyrAlaAlaSerAsnProProAlaGlnTyrSerTrpLeuIleAsnGlyThr 910              930              950
          .                .                .
TTCCAGCAAAGCACACAAGAGCTCTTTATCCCTAACATCACTGTGAATAATAGTGGATCC
PheGlnGlnSerThrGlnGluLeuPheIleProAsnIleThrValAsnAsnSerGlySer 970              990             1010
          .                .                .
TATACCTGCCACGCCAATAACTCAGTCACTGGCTGCAACAGGACCACAGTCAAGACGATC
TyrThrCysHisAlaAsnAsnSerValThrGlyCysAsnArgThrThrValLysThrIle 1030             1050             1070
          .                .                .
ATAGTCACTGATAATGCTCTACCACAAGAAAATGGCCTCTCACCTGGGGCCATTGCTGGC
IleValThrAspAsnAlaLeuProGlnGlnAsnGlyLeuSerProGlyAlaIleAlaGly 1090             1110             1130
          .                .                .
ATTGTGATTGGAGTAGTGGCCCTGGTTGCTCTGATAGCAGTAGCCCTGGCATGTTTTCTG
IleValIleGlyValValAlaLeuValAlaLeuIleAlaValAlaLeuAlaCysPheLeu 1150             1170             1190
          .                .                .
CATTTCGGGAAGACCGGCAGCTCAGGACCACTCCAATGACCCACCTAACAAGATGAATGA
HisPheGlyLysThrGlySerSerGlyProLeuGln 1210             1230             1250
          .                .                .
AGTTACTTATTCTACCCTGAACTTTGAAGCCCAGCAACCCACACAACCAACTTCAGCCTC 1270             1290             1310
          .                .                .
CCCATCCCTAACAGCCACAGAAATAATTTATTCAGAAGTAAAAAAGCAGTAATGAAACCT

1330
          .
GAAAAAAAAAAAAAAAAA
```

The present invention is also directed to a replicable recombinant cloning vehicle ("vector") having an insert comprising a nucleic acid, e.g., DNA, which comprises a base sequence which codes for a CEA peptide or a base sequence hybridizable therewith.

This invention also relates to a cell that is transformed/transfected, infected or injected with the above described replicable recombinant cloning vehicle or nucleic acid hybridizable with the aforementioned cDNA. Thus the invention also concerns the transfection of cells using free nucleic acid, without the use of a cloning vehicle.

Still further, the present invention concerns a polypeptide expressed by the above described transfected, infected or injected cell, which polypeptide exhibits immunological cross-reactivity with a CEA, as well as labelled forms of the polypeptide. The invention also relates to polypeptides having an amino acid sequence, i.e., synthetic peptides, or the expression product of a cell that is transfected, injected, infected with the above described replicable recombinant cloning vehicles, as well as labelled forms thereof. Stated otherwise, the present invention concerns a synthetic peptide having an amino acid sequence corresponding to the entire amino acid sequence or a portion thereof having no less than five amino acids of the aforesaid expression product.

The invention further relates to an antibody preparation specific for the above described polypeptide.

Another aspect of the invention concerns an immunoassay method for detecting CEA or a functional equivalent thereof in a test sample comprising (a) contacting the sample with the above described antibody preparation, and (b) determining binding thereof to CEA in the sample.

The invention also is directed to a nucleic acid hybridization method for detecting a CEA or a related nucleic acid (DNA or RNA) sample in a test sample comprising (a) contacting the test sample with a nucleic acid probe comprising a nucleic acid, which comprises a base sequence which codes for a CEA peptide sequence or a base sequence that is hybridizable therewith, and (b) determining the formation of the resultant hybridized probe.

The present invention also concerns a method for detecting the presence of carcinoembryonic antigen or a functional equivalent thereof in an animal or human patient in vivo comprising a) introducing into said patient a labeled (e.g., a radioopaque material that can be detected by X-rays, radiolabeled or labeled with paramagnetic materials that can be detected by NMR) antibody preparation according to the present invention and b) detecting the presence of such antibody preparation in the patient by detecting the label.

In another aspect, the present invention relates to the use of an antibody preparation according to the present invention for therapeutic purposes, namely, attaching to an antibody preparation radionuclides, toxins or other biological effectors to form a complex and introducing an effective amount of such complex into an animal or human patient, e.g., by injection or orally. The antibody complex would attach to CEA in a patient and the radionuclide, toxin or other biological effector would serve to destroy the CEA expressing cell.

BRIEF DESCRIPTION OF THE DRAWINGS

FIG. 1 is a schematic representation of the transmembrane CEA's.

DETAILED DESCRIPTION OF THE INVENTION

In patent applications, applicants described the following CEA's:

|  |  | ATCC No. |
|---|---|---|
| CEA-(a) | partial CEA (pcLV7) |  |
| CEA-(b) | full coding CEA (pc 15LV7) | 67709 |
| CEA-(c) | TM-1 (FL-CEA; pc 19–22) | 67710 |
| CEA-(d) | NCA (pcBT 20) | 67711 |

In the present application, applicants described the following CEA's:

|  |  | ATCC No. |
|---|---|---|
| CEA-(e) | TM-2 (pc E22) | 67712 |
| CEA-(f) | TM-3 (pc HT-6) | 67708 |
| CEA-(g) | TM-4. |  |

ATCC Nos. 67708, 67709, 67710, 67711 and 67712 were all deposited with the American Type Culture Collection on May 25, 1988.

The sequences for CEA-(a), CEA-(b), CEA-(c) and CEA-(d) are given hereinbelow:

```
CEA-(a):

GG GGT TTA CAC AAC CAC CAC CCC ATC AAA CCC TTC ATC ACC AGC AAC AAC TCC AAC CCC GTG

GAG GAT GAG GAT GCT GTA GCC TTA ACC TGT GAA CCT GAG ATT CAG AAC ACA ACC TAC CTG

TGG TGG GTA AAT AAT CAG AGC CTC CCG GTC AGT CCC AGG CTG CAG CTG TCC AAT GAC AAC

AGG ACC CTC ACT CTA CTC AGT GTC ACA AGG AAT GAT GTA GGA CCC TAT GAG TGT GGA ATC

CAG AAC GAA TTA AGT GTT GAC CAC AGC GAC CCA GTC ACC CAG CGA TTC CTC TAT GGC CCA

GAC GAC CCC ACC ATT TCC CCC TCA TAC ACC TAT TAC CGT CCA GGG GTG GAA CCT CAG CCT

CTC TGC CAT GCA GCC TCT AAC CCA CCT GCA CAG TAT TCT TGG CTG ATT GAT GGG ACC GTC

CAG CAA CAC ACA CAA GAG CTC TTT ATC TCC AAC ATC ACT GAG AAG AAC AGC GGA CTC TAT
```

-continued

```
ACC TGC CAG GCC AAT AAC TCA GCC AGT GGC ACA GCA GGA CTA CAG TCA AGA CAA TCA CAG

TCT CTG CGG ATG CCC AAG CCC TCC ATC TCC AGC AAC AAC TCC AAA CCC GTG GAG GAC AAG

GAT CGC TGT GGC CTT CAC TGT GAA CCT GAG GCT CAG AAC ACA ACC TAC CTG TGG TGG GTA

AAT GGT CAG AGC CTC CCA GTC AGT CCC AGG CTG CAG CTG TCC AAT GGC AAC AGG ACC CTC

ACT CTA TTC AAT GTC ACA AGA AAT GAC GCA AGA GCC TAT GTA TGT GGA ATC CAG AAC TCA

GTG AGT GCA AAC CGC AGT GAC CCA GTC ACC CTG GAT GTC CTC TAT GGG CCG GAC ACC CCC

ATC ATT TCC CCC CCC CC
```

| CEA-(b): |
|---|

```
           10             20             30             40             50
           *              *              *              *              *
C ACC ATG GAG TCT CCC TCU GCC CCT CTC CAC ACA TGG TGC ATC CCC TGU CAG AGG CTC
    Met Glu Ser Pre Ser Ala Pro Leu His Arg Typ Cys Ile Pro Trp Gln Arg Leu 60             70             80             90            100            110
      *              *              *              *              *              *
CTG CTC ACA OCC TCA CTT CTA ACC TTC TGG AAC CCG CCC ACC ACT GCC AAG CTC ACT
Leu Leu Thr Ala Ser Leu Leu Thr Phe Trp Asp Pro Pro Thr Thr Ala Lys Leu Thr 120            130            140            150            160            170
          *              *              *              *              *              *
ATT GAA TCC ACG CCG TTC AAT GTC GCA GAG GGC AAG GAG GTO CTT CTA CTT GTC CAC
Iln Glu Ser Thr Pro Phe Asn Val Ala Glu Gly Lys Glu Val Leu Leu Val His 180            190            200            210            220
         *              *              *              *              *
CAT CTG CCC CAG CAT CTT TTT CCC TAC AGC TGG TAC AAA GGT GAA AGA GTG CAT GGC
Asn Arg Gln Ile Ile Gly Tyr Val Ile Gly Thr Gln Gln Ala Thr Pro Gly Pro Ala 230            240            250            260            270            280
 *              *              *              *              *              *
AAC CGT CAA ATT ATA GGA TAT GTA ATA GGA ACT CAA CAA GCT ACC CCA GGG CCC GCA
Asn Arg Gln Ile Ile Gly Tyr Val Ile Gly Thr Gln Gln Ala Thr Pro Gly Pro Ala 290            300            310            320            330            340
         *              *              *              *              *              *
TAC AGT GGT CGA GAG ATA ATA TAC CCC AAT GCA TCC CTG CTG ATC CAG GAC ATC ATC
Tyr Ser Gly Arg Glu Ile Ile Tyr Pro Asn Ala Ser Leu Leu Ile Gln Asp Ile Ile 350            360            370            380            390            400
             *              *              *              *              *              *
GAG AAT GAC ACA GGA TTC TAC ACC CTA CAC GTC ATA AAG TCA GAT CTT GTG AAT CAA
Gln Asn Asp Thr Gly Phe Tyr Thr Leu His Val Ile Lys Ser Asp Leu Val Asn Gly 410            420            430            440            450
               *              *              *              *              *
GAA CCA ACA GCC CAG TTC GGG GTA TAC GGG GAG CTG CCC AAG CCC TCC ATC TCC AGC
Glu Ala Thr Gly Gln Phe Arg Val Tyr Pro Gly Leu Pro Lys Pro Ser Ile Ser Ser 460            470            480            490            500            510
 *              *              *              *              *              *
AAC AAC TCC AAA CCC GTG GAG GAC AAG CAT GCT GTG CCC TTC ACC TGT CAA CCT GAG
Asn Asn Ser Lys Pro Val Gly Asp Lys Asp Ala Val Ala Phe Thr Cys Glu Pro Glu 520            530            540            550            560            570
         *              *              *              *              *              *
ACT CAG GAC CCA ACC TAC CTG TGG TGG GTA AAC AAT CAG AAG CTC CCG CTC AGT CCC
Thr Gln Asp Ala Thr Tyr Leu Trp Trp Val Asn Asn Gln Ser Leu Pro Val Ser Pro 580            590            600            610            620
               *              *              *              *              *
AGG CTG CAG CTG TCC AAT GCC AAC AGG ACC CTC ACT CTA TTC AAT GTC ACA AGA AAT
Arg Leu Gln Leu Ser Asn Gly Asp Arg Leu Thr Leu Thr Phe Asn Val Thr Arg Asn 630            640            650            660            670            680
 *              *              *              *              *              *
GAA CAA GCA AGC TAC AAA TGT CAA ACC CAG AAC CCA GTG AGT GCC AGG CGC AGT GAT
Glu Gln Ala Ser Tyr Lys Cys Gln Thr Gln Asn Pro Val Ser Ala Arg Arg Ser Asp
```

-continued

CEA-(b):

```
        690           700           710           720           730           740
         *             *             *             *             *             *
    TCA GTC ATC CTG AAT GTC CTC TAT GGC CCG GAT GCC CCC ACC ATT TCC CCT CTA AAC
    Ser Val Ile Leu Asn Val Leu Tyr Gly Pro Asp Ala Pro Thr Ile Ser Pro Leu Asn 750           760           770           780           790
               *             *             *             *             *
    ACA TCT TAC AGA TCA GGG GAA AAT CTG AAC CTC TCC TGC CAC GCA GCC TCT AAC CCA
    Thr Ser Tyr Arg Ser Gly Glu Asn Leu Asn Leu Ser Cys His Ala Ala Ser Asn Pro 800           810           820           830           840           850
 *             *             *             *             *             *
    CCT GCA CAG TAC TCT TGG TTT GTC AAT GGG ACT TTC CAG CAA TCC ACC CAA GAG CTC
    Pro Ala Gln Tyr Ser Trp Phe Val Asn Gly Thr Phe Gln Gln Ser Thr Gln Glu Leu 860           870           880           890           900           910
          *             *             *             *             *             *
    TTT ATC CCC AAC ATC ACT GTE AAT AAT AGT GGA TCC TAT ACG TGC CAA GCC CAT AAC
    Phe Ile Pro Asn Ile Thr Val Asn Asn Ser Gly Ser Tyr Thr Cys Gln Ala His Asn 920           930           940           950           960           970
               *             *             *             *             *             *
    TCA GAC ACT GGC CTC AAT AGG ACC ACA GTC ACG ACG ATC ACA GTC TAT GCA GAG CCA
    Ser Asp Thr Gly Leu Asn Arg Thr Thr Val Thr Thr Ile Thr Val Tyr Ala Glu Pro 980           990          1000          1010          1020
                    *             *             *             *             *
    CCC AAA CCC TTC ATC ACC AGC AAC AAC TCC AAC CCC GTG GAG GAT GAG GAT GCT GTA
    Ser Asp Thr Gly Leu Asn Arg Thr Thr Val Thr Thr Ile Thr Val Tyr Ala Glu Pro 1030          1040          1050          1060          1070          1080
     *             *             *             *             *             *
    GCC TTA ACC TGT GAA CCT GAG ATT CAG AAC ACA ACC TAC CTG TGG TGG GTA AAT AAT
    Ala Leu Thr Cys Glu Pro Glu Ile Gln Asn Thr Thr Tyr Leu Trp Trp Val Asn Asn 1090          1100          1110          1120          1130          1140
                *             *             *             *             *             *
    CAG AGC CTC CCG GTC AGT CCC AGG CTG CAG CTG TCC AAT GAC AAC AGG ACC CTC ACT
    Gln Ser Leu Pro Val Ser Pro Arg Leu Gln Leu Ser Asn Asp Asn Arp Thr Leu Thr 1150          1160          1170          1180          1190
                     *             *             *             *             *
    CTA CTE AGT GTC ACA AGG AAT GAT ATA GGA CCC TAT GAG TGT GCA ATC CAG AAC GAA
    Leu Leu Ser Val Thr Arg Asn Asp Ile Gly Pro Tyr Glu Cys Ala Ile Gln Asn Asp 1200          1210          1220          1230          1240          1250
     *             *             *             *             *             *
    TTA AGT GTT GAC CAC AGC GAC CCA GTC ATC CTG AAT GTC CTC TAT GGC CCA GAC GAC
    Leu Ser Val Asp His Ser Asp Pro Val Ile Leu Asn Val Leu Tyr Gly Pro Asn Asp 1260          1270          1280          1290          1300          1310
                *             *             *             *             *             *
    CCC ACC ATT TCC CCC TCA TAC ACC TAT TAC CGT CCA GGG GTG AAC CTC AGC CTC TCC
    Pro Thr Ile Ser Pro Ser Tyr Thr Tyr Tyr Arg Pro Gly Val Asn Leu Ser Leu Ser 1320          1330          1340          1350          1360
                     *             *             *             *             *
    TGC CAT GCA GCC TCT AAC CCA CCT GCA CAG TAT TCT TGG CTG ATT CAT GGG AAC ATC
    Cys His Ala Ala Ser Asn Pro Pro Ala Gln Tyr Ser Trp Leu Ile Asp Gly Asn Ile 1370          1380          1390          1400          1410          1420
     *             *             *             *             *             *
    CAG CAA CAC ACA CAA AAG CTC TTT ATC TCC AAC ATC ACT GAG AAC AAC AGC GGA CTC
    Gln Gln His Thr Gln Glu Leu Phe Ile Ser Asn Ile Thr Glu Lys Asn Ser Gly Leu 1430          1440          1450          1460          1470          1480
                *             *             *             *             *             *
    TAT ACC TGC CAG GCC AAT AAC TCA GCC AGT GGC CAC AGC AGG ACT ACA GTC AAG ACA
    Tyr Thr Cys Gln Ala Asn Asn Ser Ala Ser Gly His Ser Arg Thr Thr Val Lys Thr 1490          1500          1510          1520          1530          1540
                     *             *             *             *             *             *
    ATC ACA GTC TCT GCG GAC GTG CCC GAG CCC TCC ATC TCC AGC AAC AAC TCC AAA CCC
    Ile Thr Val Ser Ala Asp Val Pro Lys Pro Ser Ile Ser Ser Asn Asn Ser Lys Pro 1550          1560          1570          1580          1590
```

-continued

CEA-(b):

```
      *              *              *              *              *
GTG GAG GAC AAG GAT GCT GTG GCG TTC ACC TGT GAA CCT GAG GCT CAG AAC ACA ACC
Val Glu Asp Lys Asp Ala Val Ala Phe Thr Cys Glu Pro Glu Ala Gln Asn Thr Thr 1600           1610           1620           1630           1640           1650
  *              *              *              *              *              *
TAC CTG TGG TGG GTA AAT GGT CAG AGC CTC CCA GTC AGT CCC AGG CTG CAG CTG TCC
Tyr Leu Trp Trp Val Asn Gly Gln Ser Leu Pro Val Ser Pro Arg Leu Gln Leu Ser 1660           1670           1680           1690           1700           1710
          *              *              *              *              *              *
AAT GGC AAC AGG ACC GTC ACT CTA TTC AAT GTC ACA AGA AAT GAC GCA AGA GCC TAT
Asn Gly Asn Arg Thr Val Thr Leu Phe Asn Val Thr Arg Asn Asp Ala Arg Ala Tyr 1720           1730           1740           1750           1760
               *              *              *              *              *
GTA TGT GGA ATC CAG AAC TCA GTG AGT GCA AAC CGC AGT GAC CCA GTC ACC CTG GAT
Val Cys Gly Ile Gln Asn Ser Val Ser Ala Asn Arg Ser Asp Pro Val Thr Leu Asp 1770           1780           1790           1800           1810           1820
  *              *              *              *              *              *
GTC CTC TAT GGG CCG GAC ACC CCC ATC ATT TCC CCC CCA GAC TCG TCT TAC CTT TCG
Val Leu Tyr Gly Pro Asp Thr Pro Ile Ile Ser Pro Pro Asp Ser Ser Tyr Leu Ser 1830           1840           1850           1860           1870           1880
          *              *              *              *              *              *
GGA GCG AAC CTC AAC CTC TCC TGC CAC TCA GCC TCT AAC CCA TCC CCG CAG TAT TCT
Gly Ala Asn Leu Asn Leu Ser Cys His Ser Ala Ser Asn Pro Ser Pro Gln Tyr Ser 1890           1900           1910           1920           1930
               *              *              *              *              *
TGG CGT ATC AAT GGG ATA CCG CAG CAA CAC ACA CAA GTT CTC TTT ATC GCC AAA ATC
Trp Arg Ile Asn Gly Ile Pro Gln Gln His Thr Gln Val Leu Phe Ile Ala Lys Ile 1940           1950           1960           1970           1980           1990
  *              *              *              *              *              *
ACG CCA AAT AAT AAC GGG ACC TAT GCC TGT TTT GTC TCT AAC TTG GCT ACT GGC CGC
Thr Pro Asn Asn Asn Gly Thr Tyr Ala Cys Phe Val Ser Asn Leu Ala Thr Gly Arg 2000           2010           2020           2030           2040           2050
          *              *              *              *              *              *
AAT AAT TCC ATA GTC AAG AGC ATG ACA GTC TCT GCA TCT GGA ACT TCT CCT GGT CTC
Asn Asn Ser Ile Val Lys Ser Ile Thr Val Ser Ala Ser Gly Thr Ser Pro Gly Leu 2060           2070           2080           2090           2100           2110
               *              *              *              *              *              *
TCA GCT GGG GCC ACT GTC GGC ATC ATG ATT GGA GTG CTG GTT GGG GTT GCT CTG ATA
Ser Ala Gly Ala Thr Val Gly Ile Met Ile Gly Val Leu Val Gly Val Ala Leu Ile 2120           2130           2140           2150           2160
                    *              *              *              *              *
TAG CAG CCC TGC TCT AGT TGT TGG ATT TCA GGA AAA CTG ACA GTC GTT TTG CTT CTT 2170           2180           2170           2200           2210           2220
  *              *              *              *              *              *
CCT TAA AGC ATT TGC AAC AGC TAC AGT CTA AAA TTG CTT CTT TAC CAA GGA TAT TTA 2230           2240           2250           2260           2270           2280
          *              *              *              *              *              *
CAG AAA ATA CTC TGA CCA GAG ATC GAG ACC ATC CTA GCC AAC ATC GTG AAA CCC CAT 2290           2300           2310           2320           2330
               *              *              *              *              *
CTC TAC TAA AAA TAC AAA AAT GAG CTG GGC TTG GTG GCG CGC ACC TGT AGT CCC AGT 2340           2350           2360           2370           2380           2390
  *              *              *              *              *              *
TAC TCG GGA GGC TGA GGC AGG AGA ATC GCT TGA ACC GGG AGG TGA GAT TGC AGT G 2400           2410           2420           2430           2440           2450
          *              *              *              *              *              *
AGC CCA GAT CGC ACC ACT GCA CTC CAG TCT GGC AAC AGA GCA AGA CTC CAT CTC AAA 2460           2470           2480           2490           2500
               *              *              *              *              *
AAG AAA AGA AAA GAA GAC TCT GAC CTG TAC TCT TGA ATA CAA GTT CTG GAT ACC ACT
```

-continued

CEA-(b):

```
2510          2520          2530          2540          2550          2560
  *             *             *             *             *             *
GCA CTG TCT GAG AAT TTC CAA AAC TTT AAT GAA CTA ACT GAC AGC TTC ATG AAA CTG 2570          2580          2590          2600          2610          2620
      *             *             *             *             *             *
TCC ACC AAG ATC AAG CAG AGA AAA TAA TTA ATT TCA TGG GGA CTA AAT GAA CTA ATG 2630          2640          2650          2660          2670          2680
          *             *             *             *             *             *
AGG ATA ATA TTT TCA TAA TTT TTT ATT TGA AAT TTT GCT GAT TCT TTA AAT GTC TTG 2690          2700          2710          2720          2730
              *             *             *             *             *
TTT CCC AGA TTT CAG GAA ACT TTT TTT CTT TTA AGC TAT CCA CTC TTA CAG CAA TTT 2740          2750          2760          2770          2780          2790
  *             *             *             *             *             *
GAT AAA ATA TAC TTT TGT GAA CAA AAA TTG AAA CAT TTA CAT TTT ATC CCT ATG TGG 2800          2810          2820          2830
      *             *             *             *
TCG CTC CAG ACT TGG AAA ACT ATT CAT GAA TAT TTA TAT TGT ATG
```

CEA-(c):

```
         10                  30                  50
          .                   .                   .
CAGCCGTGCTCGAAGCGTTCCTGGAGCCCAAGCTCTCCTCCACAGGTGAAGACAGGGCCA 70                  90                  110
          .                   .                   .
GCAGGAGACACCATGGGGCACCTCTCAGCCCCACTTCACAGAGTGCGTGTACCCTGGCAG
         MetGlyHisLeuSerAlaProLeuHisArgValArgValProTrpGln 130                 150                 170
          .                   .                   .
GGGCTTCTGCTCACAGCCTCACTTCTAACCTTCTGGAACCCGCCCACCACTGCCCAGCTC
GlyLeuLeuLeuThrAlaSerLeuLeuThrPheTrpAsnProProThrThrAlaGlnLeu 190                 210                 230
          .                   .                   .
ACTACTGAATCCATGCCATTCAATGTTGCAGAGGGGAAGGAGGTTCTTCTCCTTGTCCAC
ThrThrGluSerMetProPheAsnValAlaGluGlyLysGluValLeuLeuLeuValHis 250                 270                 290
          .                   .                   .
AATCTGCCCCAGCAACTTTTTGGCTACAGCTGGTACAAAGGGGAAAGAGTGGATGGCAAC
AsnLeuProGlnGlnLeuPheGlyTyrSerTrpTyrLysGlyGluArgValAspGlyAsn 310                 330                 350
          .                   .                   .
CGTCAAATTGTAGGATATGCAATAGGAACTCAACAAGCTACCCCAGGGCCCGCAAACAGC
ArgGlnIleValGlyTyrAlaIleGlyThrGlnGlnAlaThrProGlyProAlaAsnSer 370                 390                 410
          .                   .                   .
GGTCGAGAGACAATATACCCCAATGCATCCCTGCTGATCCAGAACGTCACCCAGAATGAC
GlyArgGluThrIleTyrProAsnAlaSerLeuLeuIleGlnAsnValThrGlnAsnAsp 430                 450                 470
          .                   .                   .
ACAGGATTCTACACCCTACAAGTCATAAAGTCAGATCTTGTGAATGAAGAAGCAACTGGA
ThrGlyPheTyrThrLeuGlnValIleLysSerAspLeuValAsnGluGluAlaThrGly 490                 510                 530
          .                   .                   .
CAGTTCCATGTATACCCGGAGCTGCCCAAGCCCTCCATCTCCAGCAACAACTCCAACCCT
GlnPheHisValTyrProGluLeuProLysProSerIleSerSerAsnAsnSerAsnPro 550                 570                 590
          .                   .                   .
GTGGAGGACAAGGATGCTGTGGCCTTCACCTGTGAACCTGAGACTCAGGACACAACCTAC
ValGluAspLysAspAlaValAlaPheThrCysGluProGluThrGlnAspThrThrTyr
```

-continued

```
       610                 630                 650
        .         .         .         .         .
CTGTGGTGGATAAACAATCAGAGCCTCCCGGTCAGTCCCAGGCTGCAGCTGTCCAATGGC
LeuTrpTrpIleAsnAsnGlnSerLeuProValSerProArgLeuGlnLeuSerAsnGly 670                 690                 710
        .         .         .         .         .
AACAGGACCCTCACTCTACTCAGTGTCACAAGGAATGACACAGGACCCTATGAGTGTGAA
AsnArgThrLeuThrLeuLeuSerValThrArgAsnAspThrGlyProTyrGluCysGlu 730                 750                 770
        .         .         .         .         .
ATACAGAACCCAGTGAGTGCGAACCGCAGTGACCCAGTCACCTTGAATGTCACCTATGGC
IleGlnAsnProValSerAlaAsnArgSerAspProValThrLeuAsnValThrTyrGly 790                 810                 830
        .         .         .         .         .
CCGGACACCCCCACCATTTCCCCTTCAGACACCTATTACCGTCCAGGGGCAAACCTCAGC
ProAspThrProThrIleSerProSerAspThrTyrTyrArgProGlyAlaAsnLeuSer 850                 870                 890
        .         .         .         .         .
CTCTCCTGCTATGCAGCCTCTAACCCACCTGCACAGTACTCCTGGCTTATCAATGGAACA
LeuSerCysTyrAlaAlaSerAsnProProAlaGlnTyrSerTrpLeuIleAsnGlyThr 910                 930                 950
        .         .         .         .         .
TTCCAGCAAAGCACACAAGAGCTCTTTATCCCTAACATCACTGTGAATAATAGTGGATCC
PheGlnGlnSerThrGlnGluLeuPheIleProAsnIleThrValAsnAsnSerGlySer 970                 990                 1010
        .         .         .         .         .
TATACCTGCCACGCCAATAACTCAGTCACTGGCTGCAACAGGACCACAGTCAAGACGATC
TyrThrCysHisAlaAsnAsnSerValThrGlyCysAsnArgThrThrValLysThrIle 1030                1050                1070
        .         .         .         .         .
ATAGTCACTGAGCTAAGTCCAGTAGTAGCAAAGCCCCAAATCAAAGCCAGCAAGACCACA
IleValThrGluLeuSerProValValAlaLysProGlnIleLysAlaSerLysThrThr 1090                1110                1130
        .         .         .         .         .
GTCACAGGAGATAAGGACTCTGTGAACCTGACCTGCTCCACAAATGACACTGGAATCTCC
ValThrGlyAspLysAspSerValAsnLeuThrCysSerThrAsnAspThrGlyIleSer 1150                1170                1190
        .         .         .         .         .
ATCCGTTGGTTCTTCAAAAACCAGAGTCTCCCGTCCTCGGAGAGGATGAAGCTGTCCCAG
IleArgTrpPhePheLysAsnGlnSerLeuProSerSerGluArgMetLysLeuSerGln 1210                1230                1250
        .         .         .         .         .
GGCAACACCACCCTCAGCATAAACCCTGTCAAGAGGGAGGATGCTGGGACGTATTGGTGT
GlyAsnThrThrLeuSerIleAsnProValLysArgGluAspAlaGlyThrTyrTrpCys 1270                1290                1310
        .         .         .         .         .
GAGGTCTTCAACCCAATCAGTAAGAACCAAAGCGACCCCATCATGCTGAACGTAAACTAT
GluValPheAsnProIleSerLysAsnGlnSerAspProIleMetLeuAsnValAsnTyr 1330                1350                1370
        .         .         .         .         .
AATGCTCTACCACAAGAAAATGGCCTCTCACCTGGGGCCATTGCTGGCATTGTGATTGGA
AsnAlaLeuProGlnGluAsnGlyLeuSerProGlyAlaIleAlaGlyIleValIleGly 1390                1410                1430
        .         .         .         .         .
GTAGTGGCCCTGGTTGCTCTGATAGCAGTAGCCCTGGCATGTTTTCTGCATTTCGGGAAG
ValValAlaLeuValAlaLeuIleAlaValAlaLeuAlaCysPheLeuHisPheGlyLys 1450                1470                1490
        .         .         .         .         .
ACCGGCAGGGCAAGCGACCAGCGTGATCTCACAGAGCACAAACCCTCAGTCTCCAACCAC
ThrGlyArgAlaSerAspGlnArgAspLeuThrGluHisLysProSerValSerAsnHis 1510                1530                1550
        .         .         .         .         .
ACTCAGGACCACTCCAATGACCCACCTAACAAGATGAATGAAGTTACTTATTCTACCCTG
ThrGlnAspHisSerAsnAspProProAsnLysMetAsnGluValThrTyrSerThrLeu
```

```
             1570                1590                1610
               .                   .                   .
AACTTTGAAGCCCAGCAACCCACACAACCAACTTCAGCCTCCCCATCCCTAACAGCCACA
AsnPheGluAlaGlnGlnProThrGlnProThrSerAlaSerProSerLeuThrAlaThr 1630                1650                1670
               .                   .                   .
GAAATAATTTATTCAGAAGTAAAAAAGCAGTAATGAAACCTGTCCTGCTCACTGCAGTGC
GluIleIleTyrSerGluValLysLysGln 1690                1710                1730
               .                   .                   .
TGATGTATTTCAAGTCTCTCACCCTCATCACTAGGAGATTCCTTTCCCCTGTAGGGTAGA 1750                1770                1790
               .                   .                   .
GGGGTGGGGACAGAAACAACTTTCTCCTACTCTTCCTTCCTAATAGGCATCTCCAGGCTG 1810                1830                1850
               .                   .                   .
CCTGGTCACTGCCCCTCTCAGTGTCAATAGATGAAAGTACATTGGGAGTCTGTAGGAA 1870                1890                1910
               .                   .                   .
ACCCAACCTTCTTGTCATTGAAATTTGGCAAAGCTGACTTTGGGAAAGAGGGACCAGAAC 1930                1950                1970
               .                   .                   .
TTCCCCTCCCTTCCCCTTTTCCCAACCTGGACTTGTTTTAAACTTGCCTGTTCAGAGCAC 1990                2010                2030
               .                   .                   .
TCATTCCTTCCCACCCCCAGTCCTGTCCTATCACTCTAATTCGGATTTGCCATAGCCTTG 2050                2070                2090
               .                   .                   .
AGGTTATGTCCTTTTCCATTAAGTACATGTGCCAGGAAACAGCGAGAGAGAGAAAGTAAA 2110                2130                2150
               .                   .                   .
CGGCAGTAATGCTTCTCCTATTTCTCCAAAGCCTTGTGTGAACTAGCAAAGAGAAGAAAA 2170                2190                2210
               .                   .                   .
TCAAATATATAACCAATAGTGAAATGCCACAGGTTTGTCCACTGTCAGGGTTGTCTACCT 2230                2250                2270
               .                   .                   .
GTAGGATCAGGGTCTAAGCACCTTGGTGCTTAGCTAGAATACCACCTAATCCTTCTGGCA 2290                2310                2330
               .                   .                   .
AGCCTGTCTTCAGAGAACCCACTAGAAGCAACTAGGAAAAATCACTTGCCAAAATCCAAG 2350                2370                2390
               .                   .                   .
GCAATTCCTGATGGAAAATGCAAAAGCACATATATGTTTTAATATCTTTATGGGCTCTGT 2410                2430                2450
               .                   .                   .
TCAAGGCAGTGCTGAGAGGGAGGGGTTATAGCTTCAGGAGGGAACCAGCTTCTGATAAAC 2470                2490                2510
               .                   .                   .
ACAATCTGCTAGGAACTTGGGAAAGGAATCAGAGAGCTGCCCTTCAGCGATTATTTAAAT 2530                2550                2570
               .                   .                   .
TGTTAAAGAATACACAATTTGGGGTATTGGGATTTTTCTCCTTTTCTCTGAGACATTCCA 2590                2610                2630
               .                   .                   .
CCATTTTAATTTTTGTAACTGCTTATTTATGTGAAAAGGGTTATTTTTACTTAGCTTAGC 2650                2670                2690
               .                   .                   .
TATGTCAGCCAATCCGATTGCCTTAGGTGAAAGAAACCACCGAAATCCCTCAGGTCCCTT 2710                2730                2750
```

-continued

```
GGTCAGGAGCCTCTCAAGATTTTTTTTGTCAGAGGCTCCAAATAGAAAATAAGAAAAGGT
         2770           2790           2810
          .              .              .
TTTCTTCATTCATGGCTAGAGCTAGATTTAACTCAGTTTCTAGGCACCTCAGACCAATCA
         2830           2850           2870
          .              .              .
TCAACTACCATTCTATTCCATGTTTGCACCTGTGCATTTTCTGTTTGCCCCCATTCACTT
         2890           2910           2930
          .              .              .
TGTCAGGAAACCTTGGCCTCTGCTAAGGTGTATTTGGTCCTTGAGAAGTGGGAGCACCCT
         2950           2970           2990
          .              .              .
ACAGGGACACTATCACTCATGCTGGTGGCATTGTTTACAGCTAGAAAGCTGCACTGGTGC
         3010           3030           3050
          .              .              .
TAATGCCCCTTGGGAAATGGGGCTGTGAGGAGGAGGATTATAACTTAGGCCTAGCCTCTT
         3070           3090           3110
          .              .              .
TTAACAGCCTCTGAAATTTATCTTTTCTTCTATGGGTCTATAAATGTATCTTATAATAA
         3130           3150           3170
          .              .              .
AAAGGAAGGACAGGAGGAAGACAGGCAAATGTACTTCTCACCCAGTCTTCTACACAGATG
         3190           3210           3230
          .              .              .
GAATCTCTTTGGGGCTAAGAGAAAGGTTTTATTCTATATTGCTTACCTGATCTCATGTTA
         3250           3270           3290
          .              .              .
GGCCTAAGAGGCTTTCTCCAGGAGGATTAGCTTGGAGTTCTCTATACTCAGGTACCTCTT
         3310           3330           3350
          .              .              .
TCAGGGTTTTCTAACCCTGACACGGACTGTGCATACTTTCCCTCATCCATGCTGTGCTGT
         3370           3390           3410
          .              .              .
GTTATTTAATTTTTCCTGGCTAAGATCATGTCTGAATTATGTATGAAAATTATTCTATGT
         3430           3450
          .              .
TTTTATAATAAAAATAATATATCAGACATCGAAAAAAAAAA

CEA-(d):
              10           20           30           40           50
               |            |            |            |            |
      CC GGG GGA CAC GCA GGG CCA ACA GTC ACA GCA GCC CTG ACC AGA GCA TTC CTG GAG CTC 60           70           80           90          100          110
    |            |            |            |            |            |
  AAG CTC TCT ACA AAG AGG TCG ACA GAG AAG ACA GCA GAG ACC ATG GGA CCC CCC TCA
                                                         Mel Gly Pro Pro Ser 120          130          140          150          160          170
            |            |            |            |            |            |
  GCC CCT CCC TGC AGA TTG CAT GTC CCC TGG AAG GAG GTC CTG CTC ACA GCC TCA CTT
  Ala Pro Pro Cys Arg Leu His Val Pro Trp Lys Glu Val Leu Leu Thr Ala Ser Leu 180          190          200          210          220          230
            |            |            |            |            |            |
  CTA ACC TTC TGG AAC CCA CCC ACT ACT GCC AAG CTC ACT ATT GAA TCC ACG CCA TTC
  Leu Thr Phe Trp Asn Pro Pro Thr Thr Ala Lys Leu Thr Ile Glu Ser Thr Pro Phe 240          250          260          270          280
            |            |            |            |            |
  AAT GTC GCA GAG GGG AAG GAG GTT CTA CTC GCC CAC AAC CTG CCC CAG AAT CGT
  Asn Val Ala Glu Gly Lys Glu Val Leu Leu Leu Ala His Asn Leu Pro Gln Asn Arg
```

```
        290             300             310             320             330             340
         |               |               |               |               |               |
ATT GGT TAC AGC TGG TAC AAA GGC GAA AGA GTG GAT GGC AAC AGT CTA ATT GTA GGA
Ile Gly Tyr Ser Trp Tyr Lys Gly Glu Arg Val Asp Gly Asn Ser Leu Ile Val Gly 350             360             370             380             390             400
             |               |               |               |               |               |
TAT GTA ATA GGA ACT CAA CAA GCT ACC CCA GGG CCC GCA TAC AGT GGT CGA GAG ACA
Tyr Val Ile Gly Thr Gln Gln Ala Thr Pro Gly Pro Ala Tyr Ser Gly Arg Glu Thr 410             420             430             440             450
             |               |               |               |               |
ATA TAC CCC AAT GCA TCC CTG CTG ATC CAG AAC GTC ACC CAG AAT GAC ACA GGA TTC
Ile Tyr Pro Asn Ala Ser Leu Leu Ile Gln Asn Val Thr Gln Asn Asp Thr Gly Phe 460             470             480             490             500             510
     |               |               |               |               |               |
TAC ACC CTA CAA GTC ATA AAG TCA GAT CTT GTG AAT GAA GAA GCA ACC GGA CAG TTC
Tyr Thr Leu Gln Val Ile Lys Ser Asp Leu Val Asn Glu Glu Ala Thr Gly Gln Phe 520             530             540             550             560             570
             |               |               |               |               |               |
CAT GTA TAC CCG GAG CTG CCC AAG CCC TCC ATC TCC AGC AAC AAC TCC AAC CCC GTG
His Val Tyr Pro Glu Leu Pro Lys Pro Ser Ile Ser Ser Asn Asn Ser Asn Pro Val 580             590             600             610             620
             |               |               |               |               |
GAG GAC AAG GAT GCT GTG GCC TTC ACC TGT GAA CCT GAG GTT CAG AAC ACA ACC TAC
Glu Asp Lys Asp Ala Val Ala Phe Thr Cys Glu Pro Glu Val Gln Asn Thr Thr Tyr 630             640             650             660             670             680
     |               |               |               |               |               |
CTG TGG TGG GTA AAT GGT CAG AGC CTC CCG GTC AGT CCC AGG CTG CAG CTG TCC AAT
Leu Trp Trp Val Asn Gly Gln Ser Leu Pro Val Ser Pro Arg Leu Gln Leu Ser Asn 690             700             710             720             730             740
             |               |               |               |               |               |
GGC AAC AGG ACC CTC ACT CTA CTC AGC GTC AAA AGG AAC GAT GCA GGA TCG TAT GAA
Gly Asn Arg Thr Leu Thr Leu Leu Ser Val Lys Arg Asn Asp Ala Gly Ser Tyr Glu 750             760             770             780             790             800
             |               |               |               |               |               |
TGT GAA ATA CAG AAC CCA GAG AGT GCC AAC CGC AGT GAC CCA GTC ACC CTG AAT GTC
Cys Glu Ile Gln Asn Pro Glu Ser Ala Asn Arg Ser Asp Pro Val Thr Leu Asn Val 810             820             830             840             850
             |               |               |               |               |
CTC TCT GGC CCA GAT GGC CCG ACC ATT TCC CCC TCA AAG GCC AAT TAC CGT CCA GGG
Leu Tyr Gly Pro Asp Gly Pro Thr Ile Ser Pro Ser Lys Ala Asn Tyr Arg Pro Gly 860             870             880             890             900             910
     |               |               |               |               |               |
GAA AAT CTG AAC CTC TCC TGC CAC GCA GCC TCT AAC CCA CCT GCA CAG TAC TCT TGG
Glu Asn Leu Asn Leu Ser Cys His Ala Ala Ser Asn Pro Pro Ala Gln Tyr Ser Trp 920             930             940             950             960             970
             |               |               |               |               |               |
TTT ATC AAT GGG ACG TTC CAG CAA TCC ACA CAA GAG CTC TTT ATC CCC AAC ATC ACT
Phe Ile Asn Gly Thr Phe Gln Gln Ser Thr Gln Glu Leu Phe Ile Pro Asn Ile Thr 980             990             1000            1010            1020
             |               |               |               |               |
GTG AAT AAT AGC GAA TCC TCT ATG TGC CAA GCC CAT AAC TCA GCC ACT GGC CTC AAT
Val Asn Asn Ser Glu Ser Ser Met Cys Gln Ala His Asn Ser Ala Thr Gly Leu Asn 1030            1040            1050            1060            1070            1080
 |               |               |               |               |               |
AGG ACC ACA GTC ACG ATG ATC ACA GTC TCT GGA AGT GCT CCT GTC CTC TCA GCT GTG
Arg Thr Thr Val Thr Met Ile Thr Val Ser Gly Ser Ala Pro Val Leu Ser Ala Val 1090            1100            1110            1120            1130            1140
             |               |               |               |               |               |
GCC ACC GTC GGC ATC ACG ATT GGA GTG CTG GCC AGG GTG GCT CTG ATA TAG CAG CCC
Ala Thr Val Gly Ile Thr Ile Gly Val Try Ala Arg Val Ala Leu Ile ...

1150            1160            1170            1180            1190
             |               |               |               |               |
TGG TGT ATT TTC GAT ATT TCA GGA AGA CTG GCA GAT TGG ACC AGA CCC TGA ATT CTT 1200            1210            1220            1230            1240            1250
```

-continued

```
        |            |            |            |            |            |
CTA GCT CCT CCA ATC CCA TTT TAT CCC ATG GAA CCA CTA AAA ACA AGG TCT GCT CTG 1260         1270         1280         1290         1300         1310
     |            |            |            |            |            |
CTC CTG AAG CCC TAT ATG CTG GAG ATG GAC AAC TCA ATG AAA ATT TAA AGG AAA AAC 1320         1330         1340         1350         1360         1370
        |            |            |            |            |            |
    CCT CAG GCC TGA GGT GTG TGC CAC TCA GAG ACT TCA CCT AAC TAG AGA CAG GCA AAC 1380         1390         1400         1410         1420
           |            |            |            |            |
    TGC AAA CCA AAC CTC TTT CGC TTG GCA GGA TGA TGG TGT CAT TAG TAT TTC ACA AGA 1430         1440         1450         1460         1470         1480
     |            |            |            |            |            |
AGT AGC TTC AGA GGG TAA CTT AAC AGA GTA TCA GAT CTA TCT TGT CAA TCC CAA CGT 1490         1500         1510         1520         1530         1540
        |            |            |            |            |            |
    TTT ACA TAA AAT AAG CGA TCC TTT AGT GCA CCC AGT GAC TGA CAT TAG CAG CAT CTT 1550         1560         1570         1580         1590
           |            |            |            |            |
    TAA CAC AGC CGT GTG TTC AAG TGT ACA GTG GTC CTT TTC AGA GTT GGA AAT ACT CCA 1600         1610         1620         1630         1640         1650
 |            |            |            |            |            |
ACT GAA ATG TTA AGG AAG AAG ATA GAT CCA ATT AAA AAA AAT TAA AAC CAA TTT AAA 1660         1670         1680         1690         1700         1710
     |            |            |            |            |            |
AAA AAA AAA GAA CAC AGG AGA TTC CAG TCT ACT TGA GTT AGC ATA CAG AAG TCC 1720         1730         1740         1750         1760
        |            |            |            |            |
    CCT CTA CTT TAA CTT TTA CAA AAA AGT AAC CTG AAC TAA TCT GAT GTT AAC CAA TGT 1770         1780         1790         1800         1810         1820
 |            |            |            |            |            |
ATT TAT TTG TCT GGT TCT GTT TCC TTG TTC CAG TTT GAC AAA ACC CAC TGT TCT TGT 1830         1840         1850         1860         1870         1880
     |            |            |            |            |            |
ATT GTA TTG CCC AGG GGG AGC TAT CAC TGT ACT TGT ACA GTG GTG CTG CTT TAA GTT 1890         1900         1910         1920         1930         1940
        |            |            |            |            |            |
    CAT AAA TCA CAA ATA AAA GCC AAT TAG CTC TAT AAC TAA AAA AAA AAA AAA AAA AAA 1950         1960
           |            |
    AAA AAA AAA AAA AAA AAA AAA AAA
```

A schematic relationship of the transmembrane CEA's, namely TM-1 (CEA-(c)), TM-2 (CEA-(e)), TM-3 (CEA-(f)) and TM-4 (CEA-(g)) is depicted in FIG. 1:

Assuming TM-1 is composed of five sections as depicted in FIG. 1, namely 10, 12, 14, 16 and 18, TM-2 differs from TM-1 in that the 100 amino acids (100 AA) section 14 is deleted and at splice point 20 between sections 12 and 16, surprisingly an extra amino acid, namely Asp occurs.

TM-3 is the same as TM-1 except that section 18 is truncated at splice point 22, i.e., a section of 70 amino acids is deleted and results in a new section made up of subsections 24+26. Surprisingly, however, six new amino acids (section 26) occur. Another example of formation of a novel amino acid sequences relating from a deletion of nucleic acid sequence is for platelet derived growth factor-A.

TM-4 is the same as TM-2 up until the end of subsection 24.

Subsection 24 is contained in section 18 of TM-1 and TM-2, but is not depicted in FIG. 1 for TM-1 and TM-2.

Some CEA epitopes are unique. These are the epitopes which have been useful for distinguishing the various CEA-like antigens immunologically. Peptide epitopes are defined by the linear amino acid sequence of the antigen and/or features resulting from protein folding. The information required for protein following is encoded in the primary amino acid sequence. Therefore, antigenic differences ultimately result from differences in the primary structure of the difference CEA molecules. The differences residing in the CEA protein in the CEA species can thus be determined by determining the primary amino acid sequences. This can be most readily accomplished by cloning and sequencing each of the genes for CEA. To determine which gene products will be most useful for cancer diagnosis, unique probes can be selected for each gene and expression of each gene can be determined in different tumor types by nucleic acid hybridization techniques. The present invention provides a tool with which to identify potential genes coding for different members of the CEA family and to determine the theoretical primary amino acid sequences for them. Using the method of automated peptide synthesis, peptides can then be synthesized corresponding to unique sequences in these antigens. With these peptides, antibodies to these sequences can be produced which, in the intact CEA molecule, might not be recognized by the animal being immunized. Having accomplished this, advantage can then be taken of the differences in these antigens to generate specific immunoassays for the measurement of each antigen.

A wide variety of host/cloning vehicle combinations may be employed in cloning the double-stranded nucleic acid prepared in accordance with this invention. For example, useful cloning vehicles may consist of segments of chromosomal, non-chromosomal and synthetic DNA sequences, such as various known derivatives of SV40 and known bacterial plasmids, e.g., plasmids from E. coli including col E1, pCR1, pBR322, pMB89 and their derivatives, wider host range plasmids, e.g., RP4, and phage DNAs, e.g., the numerous derivatives of phage, e.g., NM989, and other DNA phages, e.g., M13 and Filamenteous single-stranded DNA phages and vectors derived from combinations of plasmids and phage DNAs such as plasmids which have been modified to employ phage DNA or other expression control sequences or yeast plasmids such as the $2\mu$ plasmids or derivatives thereof. Useful hosts may include bacterial hosts such as strains of E. coli, such as E. coli HB 101, E. coli X1776, E. coli X2282, E. coli MRC1 and strains of Pseudomonas, Bacillus subtilis, Bacillus stearothermophilus and other E. coli, bacilli, yeasts and other fungi, animal or plant hosts such as animal (including human) or plant cells in culture or other hosts. Of course, not all hosts/vector combinations may be equally efficient. The particular selection of host/cloning vehicle combination may be made by those of skill in the art after due consideration of the principles set forth without departing from the scope of this invention.

Furthermore, within each specific cloning vehicle, various sites may be selected for insertion of the nucleic acid according to the present invention. These sites are usually designated by the restriction endonuclease which cuts them. For example, in pBR322 the Pst1 site is located in the gene for beta-lactamase, between the nucleotide triplets that code for amino acids 181 and 182 of that protein. One of the two HindII endonuclease recognition sites is between the triplets coding for amino acids 101 and 102 and one of the several Taq sites at the triplet coding for amino acid 45 of beta-lactamase in pBR322. In similar fashion, the EcoRI site and the PVUII site in this plasmid lie outside of any coding region, the EcoR1 site being located between the genes coding for resistance to tetracycline and ampicillin, respectively. These sites are well recognized by those of skill in the art. It is, of course, to be understood that a cloning vehicle useful in this invention need not have a restriction endonuclease site for insertion of the chosen DNA fragment. Instead, the vehicle could be cut and joined to the fragment by alternative means.

The vector or cloning vehicle and in particular the site chosen therein for attachment of a selected nucleic acid fragment to form a recombinant nucleic acid molecule is determined by a variety of factors, e.g., the number of sites susceptible to a particular restriction enzyme, the size of the protein to be expressed, the susceptibility of the desired protein to proteolytic degradation by host cell enzymes, the contamination of the protein to be expressed by host cell proteins difficult to remove during purification, the expression characteristics, such as the location of start and stop codons relative to the vector sequences, and other factors recognized by those of skill in the art. The choice of a vector and an insertion site for a particular gene is determined by a balance of these factors, not all sections being equally effective for a given case.

Methods of inserting nucleic acid sequences into cloning vehicles to form recombinant nucleic acid molecules include, for example, dA-dT tailing, direct ligation, synthetic linkers, exonuclease and polymerase-linked repair reactions followed by ligation, or extension of the nucleic acid strand with an appropriate polymerase and an appropriate single-stranded template followed by ligation.

It should also be understood that the nucleotide sequences or nucleic acid fragments inserted at the selected site of the cloning vehicle may include nucletodies which are not part of the actual structural gene for the desired polypeptide or mature protein or may include only a fragment of the complete structural gene for the desired protein or mature protein.

The cloning vehicle or vector containing the foreign gene is employed to transform an appropriate host so as to permit that host to replicate the foreign gene and to express the protein coded by the foreign gene or portion thereof. The selection of an appropriate host is also controlled by a number of factors recognized by the art. These include, for example, the compatibility with the chosen vector, the toxicity of proteins encoded by the hybrid plasmid, the ease of recovery of the desired protein, the expression characteristics, biosafety and costs. A balance of these factors must be struck with the understanding that not all hosts may be equally effective for expression of a particular recombinant DNA molecule.

The level of production of a protein is governed by two major factors: the number of copies of its gene within the cell and the efficiency with which those gene copies are transcribed and translated. Efficiency of transcription and translation (which together comprise expression) is in turn dependent upon nucleotide sequences, normally situated ahead of the desired coding sequence. These nucleotide sequences or expression control sequences define inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to other known expression control sequences as as to favor higher levels of expression. This having been achieved, the newly engineered nucleic acid, e.g., DNA, fragment may be inserted into a multicopy plasmid or a bacteriophage derivative in order to increase the number of gene copies within the cell and thereby further improve the yield of expressed protein.

Several expression control sequences may be employed as described above. These include the operator, promoter and robosome binding and interaction sequences (including sequences such as the Shine-Dalgarno sequences) of the lactose operon of E. coli ("the lac system"), the corresponding sequences of the tryptophan synthetase system of E. coli ("the trp system"), the major operator and promoter regions of phage λ ($O_L P_L$ and $O_R P'_R$), the control region of Filamenteous single-stranded DNA phages, or other sequences which control the expression of genes of prokaryotic or eukaryotic cells and their viruses. Therefore, to improve the production of a particular polypeptide in an appropriate host, the gene coding for that polypeptide may be selected and removed from a recombinant nucleic acid molecule containing it and reinserted into a recombinant nucleic acid molecule closer or in a more appropriate relationship to its former expression control sequence or under the control of one of the above described expression control sequences. Such methods are known in the art.

as used herein "relationship" may encompass many factors, e.g., the distance separating the expression enhancing and promoting regions of the recombinant nucleic acid molecule and the inserted nucleic acid sequence, the transcription and translation characteristics of the inserted nucleic acid sequence or other sequences in the vector itself, the particular nucleotide sequence of the inserted nucleic acid sequence and other sequences of the vector and the particular characteristics of the expression enhancing and promoting regions of the vector.

Further increases in the cellular yield of the desired products depend upon an increase in the number of genes that can be utilized in the cell. This is achieved, for illustration purposes, by insertion of recombinant nucleic acid molecules engineered into the temperate bacteriophage λ (NM989), most simply by digestion of the plasmid with a restriction enzyme, to give a linear molecule which is then mixed with a restricted phage λ cloning vehicle (e.g., of the type described by N. E. Murray et al, "Lambdoid Phages That Simplify the Recovery of In Vitro Recombinants", *Molec. Gen. Genet.*, 150, pp. 53–61 (1977) and N. E. Murray et al, "Molecular Cloning of the DNA Ligase Gene From Bacteriophage T4", *J. Mol. Biol.*, 132, pp. 493–505 (1979)) and the recombinant DNA molecule recircularized by incubation with DNA ligase. The desired recombinant phage is then selected as before and used to lysogenize a host strain of *E. coli*.

Particularly useful λ cloning vehicles contain a temperature-sensitive mutation in the repression gene cI and suppressible mutations in gene S, the product of which is necessary for lysis of the host cell, and gene E, the product of which is major capsid protein of the virus. With this system, the lysogenic cells are grown at 32° C. and then heated to 45° C. to induce excision of the prophage. Prolonged growth at 37° C. leads to high levels of production of the protein, which is retained within the cells, since these are not lysed by phage gene products in the normal way, and since the phage gene insert is not encapsulated it remains available for further transcription. Artificial lysis of the cells then releases the desired product in high yield.

In addition, it should be understood that the yield of polypeptides prepared in accordance with this invention may also be improved by substituting different codons for some or all of the codons of the present DNA sequences, these substituted codons coding for amino acids identical to those codes for by the codons replaced.

Finally, the activity of the polypeptides produced by the recombinant nucleic acid molecules of this invention may be improved by fragmenting, modifying or derivatizing the nucleic acid sequences or polypeptides of this invention by well-known means, without departing from the scope of this invention.

The polypeptides of the present invention include the following:

(1) the polypeptides expressed by the above described cells, (2) polypeptides prepared by synthetic means, (3) fragments of polypeptides (1) or (2) above, such fragments produced by synthesis of amino acids or by digestion or cleavage.

Regarding the synthetic peptides according to the invention, chemical synthesis of peptides is described in the following publications: S. B. H. Kent, *Biomedical Polymers*, eds. Goldberg, E. P. and Nakajima, A. (Academic Press, New York), 213–242, (1980); A. R. Mitchell, S. B. H. Kent, M. Engelhard and R. B. Merrifield, *J. Org. Chem.*, 43, 2845–2852, (1978); J. P. Tam, T. -W. Wong, M. Riemen, F. -S. Tjoeng and R. B. Merrifield, *Tet. Letters*, 4033–4036, (1979); S. Mojsov, A. R. Mitchell and R. B. Merrifield, *J. Org. Chem.*, 45, 555–560, (1980); J. P. Tam, R. D. DiMarchi and R. B. Merrifield, *Tet. Letters*, 2851–2854, (1981); and S. B. H. Kent, M. Riemen, M. Le Doux and R. B. Merrifield, *Proceedings of the IV International Symposium on Methods of Protein Sequence Analysis*, (Brookhaven Press, Brookhaven, NY), in press, 1981.

In the Merrifield solid phase procedure, the appropriate sequence of L-amino acids is built up form the carboxyl terminal amino acid to the amino terminal amino acid. Starting with the appropriate carboxyl terminal amino acid attached to a polystyrene (or other appropriate) resin via chemical linkage to a chloromethyl group, benzhydrlamine group, or other reactive group of the resin, amino acids are added one by one using the following procedure. The peptide-resin is:

(a) washed with methylene chloride;

(b) neutralized by making for 10 minutes at room temperature with 5% (v/v) diisopropylethylamine (or other hindered base) in methylene chloride;

(c) washed with methylene chloride;

(d) an amount of amino acid equal to six times the molar amount of the growing peptide chain is activated by combining it with one-half as many moles of a carbodiimide (e.g., dicyclohexylcarbodiimide, or diiospropylcarbodiimide) for ten minutes at 0° C., to form the symmetric anhydride of the amino acid. The amino acid used should be provided originally as the N-alpha-tert.-butyloxycarbonyl derivative, with side chains protected with benzyl esters (e.g., aspartic or glutamic acids), benzyl ethers (e.g., serine, threonine, cysteine or tyrosine), benzyloxcarbonyl groups (e.g, lysine) or other protecting groups commonly used in peptide synthesis;

(e) the activated amino acid is reacted with the peptide-resin for two hours at room temperature, resulting in addition of the new amino acid to the end of the growing peptide chain;

(f) the peptide-resin is washed with methylene chloride;

(g) the N-alpha-(tert.-butyloxycarbonyl) group is removed from the most recently added amino acid by reacting with 30 to 65%, preferably 50% (v/v) trifluoroacetic acid in methylene chloride for 10 to 30 minutes at room temperature;

(h) the peptide-resin is washed with methylene chloride;

(i) steps (a) through (h) are repeated until the required peptide sequence has been constructed.

The peptide is then removed from the resin and simultaneoulsy the side-chain protecting groups are removed, by reaction with anhydrous hydrofluoric acid containing 10% v/v of anisole or other suitable (aromatic) scavenger. Subsequently, the peptide can be purified by gel filtration, ion exchange, high pressure liquid chromatography, or other suitable means.

In some cases, chemical synthesis can be carried out without the sold phase resin, in which case the synthetic reactions are performed entirely in solution. The reactions are similar and well known in the art, and the final product is essentially identical.

Digestion of the polypeptide can be accomplished by using proteolytic enzymes, especially those enzymes whose substrate specificity results in cleavage of the polypeptide at sites immediately adjacent to the desired sequence of amino acids.

Cleavage of the polypeptide can be accomplished by chemical means. Particular bonds between amino acids can be cleaved by reaction with specific reagents. Examples include the following: bonds involving methionine are cleaved by cyanogen bromide; asparaginyl-glycine bonds are cleaved by hydroxylamine.

The present invention has the following advantages:

(1) The nucleic acids coding for TM-1, TM-2 and TM-3 can be used as probes to isolate other members of the CEA gene family.

(2) The nucleic acids coding for TM-1, TM-2 and TM-3 can be used to derive oligonucleotide probes to determine the expression of TM-1, TM-2, TM-3 and other CEA genes in various tumor types.

(3) TM-1, TM-2, TM-3 and TM-4 nucleotide sequences can be used to predict the primary amino acid sequence of the protein for production of synthetic peptides.

(4) Synthetic peptides derived from the above sequence can be used to produce sequence-specific antibodies.

(5) Immunoassays for each member of the CEA antigen family can be produced with these sequence-specific antibodies and synthetic peptides.

(6) The aforementioned immunoassays can be used as diagnostics for different types of cancer if it is determined that different members of the CEA family are clinically useful markers for different types of cancer.

Peptides according to the present invention can be labelled by conventional means using radioactive moieties (e.g., $^{125}$I), enzymes, dyes and fluorescent compounds, just to name a few.

Several possible configurations for immunoassays according to the present invention can be used. The readout systems capable of being employed in these assays are numerous and non-limiting examples of such systems include fluorescent and colorimetirc enzyme systems, radioisotopic labelling and detection and chemiluminescent systems. Two examples of immunoassay methods are as follows:

(1) An enzyme linked immunoassay (ELISA) using an antibody preparation according to the present invention (including Fab or F(ab)' fragments derived therefrom) to a solid phase (such as a microtiter plate or latex beads) is attached a purified antibody of a specificity other than that which is conjugated to the enzyme. This solid phase antibody is contacted with the sample containing CEA antigen family members. After washing, the solid phase antibody-antigen complex is contacted with the conjugated anti-peptide antibody (or conjugated fragment). After washing away unbound conjugate, color or fluorescence is developed by adding a chromogenic or fluorogenic substrate for the enzyme. The amount of color or fluorescence developed is proportional to the amount of antigen in the sample.

(2) A competitive fluorometric immunoassay using fluorescently labelled peptide or synthetic peptides of the sequences for TM-2, TM-2, TM-3 and TM-4. In this example, the purified peptide expressed by cells or synthetic peptides thereof are fluorescently labelled. To a solid phase is attached a purified antibody. This solid phase is then contacted with sample containing CEA antigen family members to which has been added fluorescent peptide probe. After binding, excess probe is washed away the amount of bound probe is quantitated. The amount of bound fluorescent probe will be inversely proportional to the amount of antigen in the sample.

In the nucleic acid hybridization method according to the present invention, the nucleic acid probe is conjugated with a label, for example, an enzyme, a fluorophore, a radioisotope, a chemiluminescent compound, etc. In the most general case, the probed would be contacted with the sample and the presence of any hybridizable nucleic acid sequence would be detected by developing in the presence of a chromogenic enzyme substrate, detection of the fluorophore by epifluorescence, by autoradiography of the radioisotopically labelled probed or by chemiluminescence. The detection of hybridizable RNA sequences can be accomplished by (1) a dot blot methodology or (2) an in sutu hybridization methodology. Methods for these last two techniques are described by D. Gillespie and J. Bresser, "mRNA Immobilization in NaI: Quick Blots", *Biotechniques*, 184–192, November/December 1983 and J. Lawrence and R. Singer, "Intracellular Localization of Messenger RNAs for Cytosketal Proteins", *Cell*, 45, 407–415, May 9, 1986, respectively. The readout systems can be the same as described above, e.g., enzyme labelling, radiolabelling, etc.

As stated above, the invention also relates to the use in medicine of the aforementioned complex of the invention.

The invention further provides a pharmaceutical composition containing as an active ingredient a complex of the invention in the form of a sterile and/or physiologically isotonic aqueous solution.

For parenteral administration, solutions and emulsions containing as an active ingredient the complex of the invention should be sterile and, if appropriate, blood-isotonic.

It is envisaged that the active complex will be administered perorally, parenterally (for example, intramuscularly, intraperitoneally, or intravenously), rectally or locally.

EXAMPLE 1

Preparation of cDNA in pcE22 which codes for TM2-CEA [CEA-(e)]

EXAMPLE 1a

RNA Preparation

Messenger RNA was prepared by the proteinase K extraction method of J. Favolaro, R. Treisman and R. Kamen, *Methods in Enzymology*, 65, 718, Academic Press, Inc. (1980), followed by oligo dT cellulose chromatography to yield poly A+ RNA (3'-polyadenylated eukaryotic RNA containing most mRNA sequences that can be translated into polypeptides). To obtain approximately 100 μg of poly A+ RNA, approximately 3×10$^8$ cells of transfectant 23.411 (ATCC No. CRL 9731, deposited with the ATCC on Jun. 1, 1988), that expressed TM-1, TM-2, TM-3 and TM-4, Kamarck et al, *Proc. Natl. Acad. Sci., USA*, 84, 5350–5354, August 1987, were harvested from roller bottles after late logarithmic growth. Cells were lysed by homogenization in an ice-cold solution of 140 mM Nacl, 1.5 mM MgCl$_2$, 10 mM Tris-HCl, pH 8.0, 0.5% NP40, 4 mM dithiothreitol and 20 units of placental ribonuclease inhibitor/ml. sodium deoxycholate was then added to 0.2%. Cytoplasm and nuclei were separated by centrifugation of the homogenate at 12,000 xg for 20 minutes. The cytoplasmic fraction was mixed with an equal volume of 0.2 M tris-HCl, pH 7.8, 23 mM EDTA, 0.3 M NaCl, 2% sodium dodecyl sulfate and 400 μg/ml of proteinase K, incubated for 1 hour at 37° C., then extracted once with an equal volume of phenol/cholorform (1:1/v:v) solution. Nucleic acids were obtained by ethanol precipitation of the separated aqueous phase. Total RNA was enriched by passage in 0.5 M NaCl, 10 mM Tris-HCl, pH 7.8, 0.1% sarcosyl through an oligo dT(12–18) cellulose column. After washing, bound RNA was eluted in the same solution without sodium chloride.

EXAMPLE 1b

Reverse Transcription of mRNA

Ten micrograms of poly A+ RNA were primed for reverse transcription with oligo dT(12–18) and pdN$_6$ primers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids was replaced with the second complementary strand by treatment with RNase H, *E. coli* DNA polymerase I and *E. coli* DNA ligase at 12° C. and 22° C. for 1.5 hours each. Molecular ends were polished by treatment with T4 DNA polymerase. cDNA was phenol/chloroform extracted and purified over a "SEPHADEX G-50" spun column prepared in 10 mM Tris-HCl, ph 7.8, 1 mM EDTA (TE).

EXAMPLE 1c

Cloning of pcE22 (plasmid cDNA E22)

Synthetic DNA linkers

5' pCCCGGG 3'

3' GGGCCCTTAA 5' were attached to the ends of cDNA by blunt end ligation with excess T4 DNA ligase. Excess linkers were removed by chromatography through "SEPHADEX G-50" (medium) in TE, and by fractionation on 0.8% low melting agarose gel. Based on Northern blot analysis of poly A+ RNA of the 23.411 cell line, the size of the CEA-related mRNA was estimated at 3.6 kb. Therefore, cDNA fragments between 2 and 4 kb were recovered from gel slices and fragments were ethanol precipiated. After resuspension of cDNA in TE, EcoRI-cleaved lambada gt10 arms were added to cDNA at an estimated molar ration of 1:1. Ligation proceeded at 7° C. for 2 days in the presence of T4 DNA ligase. Aliquots of the ligation reaction were added to commercially-obtained packaging mix (Stratagene, San Diego, Calif. U.S.A.). Five million phage particles were obtained often in vitro packaging and infection of *E. coli* host NM514.

EXAMPLE 1d

Screening of Recombinant Library

Five hundred thousand packaged lambda particles were plated on lawns of *E. coli* NM514 and replicate patterns were lifted onto nitrocellulose sheets as described by W. D. Benton and R. W. Davis, *Science* 196, 180–182, (1977). Positive phage were selected by hybridization with $^{32}$P-labeled LV7 cDNA insert probe that contained a domain repeated amoung various CEA family members. By multiple rounds of screening. Phage from individual plaques were amplified and titered, and these were used to prepare small quantities of recombinant phage DNA.

EXAMPLE 1e

DNA Manipulation

Phage DNA was prepared according to T. Maniatis, E. Fritsch and J. Sambrook, *Molecular Cloning, A Laboratory Manual*, Cold Spring Harbor, (1982). DNA segments were isolated from low melting agarose gels and inserted for subcloning into Bluescript plasmid vectors (Stratagene, San Diego, Calif. U.S.A.). DNA sequencing was performed by the dideoxy termination method of F. Sanger, S. Nicklen and A. Coulson, *Proc. Natl. Acad. Sci., U.S.A.*, 74, 5463–5467, (1977). The nucleic acid and translated sequence for cDNA in pcE22 is given hereinabove (TM-2 (CEA-(e)).

EXAMPLE 2

Preparation of cDNA in pcHT-6 which Partically Codes for TM3-CEA [CEA-(f)]

EXAMPLE 2a

RNA Preparation

Messenger RNA was prepared by the proteinase K extraction method of J. Favolaro, R. Treisman and R. Kamen, *Methods in Enzymology*, 65 718, Academic Press, Inc. (1980), followed by oligo dT cellulose chromatography to yield poly A+ RNA (3'-poladenylated eukaryotic RNA containing most mRNA sequences that can be translated into polypeptides). To obtain approximately 100 μg of poly A+ RNA, approximately 3×10$^8$ cells of HT-29 tumor cells (ATCC HTB38) were harvested form roller bottles after late logarithmic growth. Cells were lysed by homogenization in an ice-cold solution of 140 mM NaCl, 1.5 mM MgCl$_2$, 10 mM Tris-HCl, pH 8.0, 0.5% NP40, 4 mM dithiothreitol and 20 units of placental ribonuclease inhibitor/ml. Sodium deoxycholate was then added to 0.2%. Cytoplasm and nuclei were separated by centriguation of the homogenate at 12,000×g for 20 minutes. The cytoplasmic fraction was mixed with an equal volume of 0.2 M tris-Hcl, pH 7.8, 25 mM EDTA, 0.3 M NaCl, 2% sodium dodecyl sulfate and 400 μg/ml of proteinase K, incubated for 1 hour at 37° C., then extracted once with an equal volume of phenol/choloform (1:1/v:v) solution. Nucleic acids were obtained by ethanol precipitation of the separated aqueous phase. Total RNA was enriched by passage in 0.5 M NaCl, 10 mM Tris-HCl, pH 7.8, 0.1% sarcosyl through an oligo dT(12–18) cellulose column. After washing, bound RNA was eluted in the same solution without sodium chloride.

EXAMPLE 2b

Reverse Transcription of mRNA

Ten micrograms of HT-29 poly A+ RNA were primed for reverse transcription with oligo dT(12–18) and pdN$_6$ primers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids was replaced with the second complementary strand by treatment with RNase H, *E. coli* DNA polymerase I and *E. coli* DNA ligase at 12° C. and 22° C. for 1.5 hours each. Molecular ends were polished by treatment with T4 DNA polymerase. cDNA was phenol/chloroform extracted and purified over a "SEPHADEX G-50" spun column prepared in 10 mM Tris-HCl, pH 7.8, 1 mM EDTA (TE).

EXAMPLE 2c

Cloning of pcHT-6 (plasmid cDNA HT-6)

Synthetic DNA linkers

5' pCCCGGG 3'

3' GGGCCCTTAA 5' were attached to the ends of cDNA by blunt end ligation with excess T4 DNA ligase. Excess linkers were removed by chromatography through "SEPHADEX G-50" (medium) in TE, and by fractionation on 0.8% low melting agarose gel. Based on Northern blot analysis of poly A+ RNA of the HT-29 cell line, the size of the CEA-related mRNA was estimated at 2.2 kb. Therefore, cDNA fragments between 2 and 3 kb were recovered from gel slices and fragments were ethanol precipitated. After suspension of cDNA in TE, EcoRI-cleaved lambada gt10 arms were added to cDNA at an estimated molar ratio of 1:1. Ligation proceeded at 7° C. for 2 days in the presence of T4 DNA ligase. Aliquots of the ligation reaction were added to commercially-obtained packaging mix (Stratagene, San Diego, Calif., U.S.A.). Five million phage particles were obtained often in vitro packaging and infection of E. coli host NM514.

EXAMPLE 2d

Screening of Recombinant Library

Five hundred thousand packaged lambda particles were plated on lawns of E. coli NM514 and replicate patterns were lifted onto nitrocellulose sheets as described by W. D. Benton and R. W. Davis, Science, 196, 180–182, (1977). Positive phage were selected by hybridization with $^{32}$P-labeled LV7 cDNA insert probe that contained a domain repeated amoung various CEA family members. By multiple rounds of screening. Phage from individual plaques were amplified and titered, and these were used to prepare small quantities of recombinant phage DNA.

EXAMPLE 2e

DNA Manipulation

Phage DNA was prepared according to T. Maniatis, E. Fitsch and J. Sambrook, Molecular Cloning, A Laboratory Manual, Cold Spring Habor, (1982). DNA segments were isolated from low melting agarose gels and inserted for subcloning into Bluescript plasmid vectors (Stratagene, San Diego, Calif., U.S.A.). DNA sequencing was performed by the didexoy termination method of F. Sanger, S. Nicklen and A. Coulson, Proc. Natl. Acad. Sci., U.S.A., 74, 5463–5467, (1977). The nucleic acid and translated sequence for cDNA in HT-6 not complete at the 5' end of it s coding region, but the nucleotide sequence and restricting map of the HT-6 insert indicates that it is related to nucleic acid sequences of cDNA clones coding for CEA-(c) and CEA-(e). The nucleotide sequence of HT-6 insert differs from these clones at only nucleotide position 1463 to 1515 and 1676 to 2429 of the CEA-(c) cDNA. It is inferred from this result that the pcHT-6 insert is a partial coding sequence for CEA-(f) and the presumed nucleic acid and translated sequence of CEA-(f) is given hereinabove (TM-3 (CEA-(f)).

EXAMPLE 3

Preparation of cDNA which codes for TM4-CEA [CEA-(g)]

EXAMPLE 3a

RNA Preparation

Messenger RNA is prepared by the proteinase K extraction method of J. Favolaro, R. Treisman and R. Kamen, Methos in Enzymology, 65, 718, Academic Press, Inc. (1980), followed by oligo dT cellulose chromatography to yield poly A+ RNA (3'-polyadenylated eukaryotic RNA containing most mRNA sequences that can be translated into polypeptides). To obtain approximately 100 μg of poly A+ RNA, approximately 3×10$^8$ cells of transfectant 23.411 or tumor cell line HT-29 (ATCC HTB 38) are harvested from roller bottles after late logarithmic growth. Cells are lysed by homogenization in an ice-cold solution of 140 mM NaCl, 1.5 mM MgCl$_2$, 10 mM Tris-HCl, pH 8.0, 0.5% NP40, 4 mM dithiothreitol and 20 units of placental ribonuclease inhibitor/ml. Sodium deoxycholate was then added to 0.2%. Cytoplasm and nuclei are separated by centriguation of the homongenate at 12,000×g for 20 minutes. The cytoplasmic fraction is mixed with an equal volume of 0.2 M Tris-Hcl, pH 7.8, 25 mM EDTA, 0.3 M NaCl, 2% sodium dodecyl sulfate and 400 μg/ml of proteinase K, incubated for 1 hour at 37° C., then extracted once with an equal volume of phenol/cholorform (1:1/v:v) solution. Nucleic acids are obtained by ethanol precipitation of the separated aqueous phase. Total RNA is enriched by passage in 0.5 M NaCl, 10 mM Tris-HCl, pH 7.8, 0.1% sarcosyl through an oligo dT(12–18) cellulose column. After washing, bound RNA is eluted in the same solution without sodium chloride.

EXAMPLE 3b

Reverse Transcription of mRNA

Ten micrograms of 23.411 or HT 29 poly A+ RNA are primed for reverse transcription with oligo dT(12–18) and pdN$_6$ primers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids is replaced with the second complementary strand by treatment with RNase H, E. coli DNA polymerase I and E. coli DNA ligase at 12° C. and 22° C. for 1.5 hours each. Molecular ends are polished by treatment with T4 DNA polymerase. cDNA is phenol/cholorform extracted and purified over a "SEPHADEX G-50" spun column prepared in 10 mM Tris-HCl, pH 7.8, 1 mM EDTA (TE).

EXAMPLE 3c

Cloning of cDNA for CEA-(g)

Synthetic DNA linkers

5' pCCCGGG 3'

3' GGGCCCTTAA 5' are attached to the ends of cDNA by blunt end ligation with excess T4 DNA ligase. Excess linkers are removed by chromatography through "SEPHADEX G-50" (medium) in TE, and by fractionation on 0.8% low melting agarose gel. Based on Northern blot analysis of poly A+ RNA of the 23.411 and HT-29 cell lines, the size of the CEA-related mRNA is estimated at 1.7 kb. Therefore, cDNA fragments between 1 and 2 kb are recovered from gel slices and fragments are ethanol precipitated. After resuspension of cDNA in TE, EcoRI-cleaved lambda gt10 arms are added to cDNA at an estimated molar ration of 1:1. Ligation proceeds at 7° C. for 2 days in the presence of T4 DNA ligase. Aliquots of the ligation reaction are added to commercially-obtained packaging mix (Stratagene, San Diego, Calif., U.S.A.). Phage particles are obtained after in vitro packaging and infection of E. coli host NM514.

EXAMPLE 3d

Screening of Recombinant Library

Five hundred thousand to one million packaged lambda particles are plated on lawns of E. coli NM514 and replicate patterns are lifted onto nitrocellulose sheets as described by W. D. Benton and R. W. Davis, *Science*, 196, 180–182, (1977). Positive phage are selected by hybridization with $^{32}$P-labeled LV7 cDNA insert probe that contained a domain repeated amoung various CEA family members. By this selection method, positive phage are obtained after multiple rounds of screening. Phage form individual plagues are amplified and titered, and these are used to prepare small quantities of recombinant phage DNA.

EXAMPLE 3e

DNA Manipulation

Phage DNA is prepared according to T. Maniatis, E. Fritsch and J. Sambrook, *Molecular Cloning, A Laboratory Manual*, Cold Spring Harbor, (1982). DNA segments are isolated from low melting agarose gels and inserted for subcloning into Bluescript plasmid vectors (Stratagene, San Diego, Calif., U.S.A.). DNA sequencing is performed by the didexoy termination method of F. Sanger, S. Nicklen and A. Coulson, *Proc. Natl. Acad. Sci., U.S.A.*, 74, 5463–5467, (1977). The nucleotide and translated sequence for a cDNA coding for CEA-(g) is given hereinabove (TM-4 (CEA-(g)).

EXAMPLE 4

Screening of a KG-1 cDNA Library with $^{32}$P-labelled CEA Probe, LV7 (CEA-(A))

A segment of cDNA coding for a portion of carcinoembroynic antigen [LV7 or CEA-(a)] was radiolabelled by random priming and used to detect homologous sequences on filter replicas of a commercial cDNA library prepared from KG-1 cells in bacteriophage vector λ gt11 (Clontech Laboratories, Inc., Palo Alto, Calif., U.S.A.). Hybridizations were performed at 68° C. in 2×SSSPE (1×SSPE—0.15 M NaCl, 0.01 M sodium phosphate and 1 mM EDTA, pH 7), 5×Denhart's solution and 100 μg of denatured salmon sperm DNA per ml, and post-hybridization washes were in 0.2× SSC, 0.25% sodium dodecyl sulfate.

Positive phage were picked, rescreened to homogeneity, and amplified for production of DNA. cDNA inserts were excised from phage DNA with EcoRI endonuclease and subcloned into the EcoRI site of the plasmid vector pBluescript KS. DNA sequencing on double-stranded DNA was by the method of Sanger et al, supra. The sequences of two different inserts from the KG-1 cDNA library are shown below:

```
pcKGCEA1:

1 acagcacagctgacagccgtactcaggaagcttctggatcctaggcttatctccacagag    60

61 gagaacacacaagcagcagagaccatgggcccctctcagcccctccctgcacacacctc   120
                                 MetGlyProLeuSerAlaProProCysThrHisLeu 121 atcacttggaagggggtcctgctcacagcatcacttttaaacttctggaatccgcccaca   180
    IleThrTrpLysGlyValLeuLeuThrAlaSerLeuLeuAsnPheTrpAsnProProThr 181 actgcccaagtcacgattgaagcccagccacccaaagtttctgaggggaaggatgttctt   240
    ThrAlaGlnValThrIleGluAlaGlnProProLysValSerGluGlyLysAspValLeu 241 ctacttgtccacaatttgccccagaatcttgctggctacatttggtacaaagggcaaatg   300
    LeuLeuValHisAsnLeuProGlnAsnLeuAlaGlyTyrIleTrpTyrLysGlyGlnMet 301 acatacgtctaccattacattacatcatatgtagtagacggtcaaagaattatatatggg   360
    ThrTyrValTyrHisTyrIleThrSerTyrValValAspGlyGlnArgIleIleTyrGly 361 cctgcatacagtggaagagaaagagtatattccaatgcatccctgctgatccagaatgtc   420
    ProAlaTyrSerGlyArgGluArgValTyrSerAsnAlaSerLeuLeuIleGlnAsnVal 421 acgcaggaggatgcaggatcctacaccttacacatcataaagcgacgcgatgggactgga   480
    ThrGlnGluAspAlaGlySerTyrThrLeuHisIleIleLysArgArgAspGlyThrGly 481 ggagtaactggacatttcaccttcaccttacacctggagactcccaagccctccatctcc   540
    GlyValThrGlyHisPheThrPheThrLeuHisLeuGluThrProLysProSerIleSer 541 agcagcaacttaaatcccagggaggccatggaggctgtgatcttaacctgtgatcctgcg   600
    SerSerAsnLeuAsnProArgGluAlaIleGluAlaValIleLeuThrCysAspProAla 601 actccagccgcaagctaccagtggtggatgaatggtcagagcctccctatgactcacagg   660
    ThrProAlaAlaSerTyrGlnTrpTrpMetAsnGlyGlnSerLeuProMetThrHisArg 661 ttgcagctgtccaaaaccaacaggaccctctttatatttggtgtcacaaagtatattgca   720
    LeuGlnLeuSerLysThrAsnArgThrLeuPheIlePheGlyValThrLysTyrIleAla 721 ggaccctatgaatgtgaaatacggaacccagtgagtgccagccgcagtgacccagtcacc   780
    GlyProTyrGluCysGluIleArgAsnProValSerAlaSerArgSerAspProValThr 781 ctgaatctcctcccaaagctgtccaagccctacatcacaatcaacaacttaaacccccaga   840
    LeuAsnLeuLeuProLysLeuSerLysProTyrIleThrIleAsnAsnLeuAsnProArg 841 gagaataaggatgtcttaaccttcacctgtgaacctaagagtgaaactacacctacatt   900
    GluAsnLysAspValLeuThrPheThrCysGluProLysSerGluAsnTyrThrTyrIle 901 tggtggctaaatggtcagagcctccctgtcagtcccagggtaaagcgacccattgaaaac   960
    TrpTrpLeuAsnGlyGlnSerLeuProValSerProArgValLysArgProIleGluAsn 961 aggatcctcattctacccaatgtcacgagaaatgaaacaggaccttatcaatgtgaaata  1020
```

-continued

```
                 ArgIleLeuIleLeuProAsnValThrArgAsnGluThrGlyProTyrGlnCysGluIle 1021 cgggaccgatatggtggcatccgcagtgacccagtcaccctgaatgtcctctatggtcca   1080
     ArgAspArgTyrGlyGlyIleArgSerAspProValThrLeuAsnValLeuTyrGlyPro 1081 gacctccccagcatttacccttcattcacctattaccgttcaggagaaaacctctacttt   1140
     AspLeuProSerIleTyrProSerPheThrTyrTyrArgSerGlyGluAsnLeuTyrPhe 1141 tcctgcttcggtgagtctaacccacgggcacaatattcttggacaattaatgggaagttt   1200
     SerCysPheGlyGluSerAsnProArgAlaGlnTyrSerTrpThrIleAsnGlyLysPhe 1201 cagctatcaggacaaaagctctctatcccccaataactacaaagcatagtgggctctat    1260
     GlnLeuSerGlyGlnLysLeuSerIleProGlnIleThrThrLysHisSerGlyLeuTyr 1261 gcttgctctgttcgtaactcagccactggcaaggaaagctccaaatccatcacagtcaaa   1320
     AlaCysSerValArgAsnSerAlaThrGlyLysGluSerSerLysSerIleThrValLys 1321 gtctctgactggatattaccctgaattctactagttcctccaattccattttctcccatg   1380
     ValSerAspTrpIleLeuProEnd 1381 gaatcacgaagagcaagacccactctgttccagaagccctataatctggaggtggacaac   1440

1441 tcgatgtaaatttcatgggaaaaccttgtacctgacatgtgagccactcagaactcacc   1500

1501 aaaatgttcgacaccataacaacagctactcaaactgtaaaccaggataagaagttgatg   1560

1561 acttcacactgtggacagttttttcaaagatgtcataacaagactccccatcatgacaagg   1620

1621 ctccaccctctactgtctgctcatgcctgcctctttcacttggcaggataatgcagtcat   1680

1681 tagaatttcacatgtagtagcttctgagggtaacaacagagtgtcagatatgtcatctca   1740

1741 acctcaaacttttacgtaacatctcagggaaatgtggctctctccatcttgcatacaggg   1800

1801 ctcccaatagaaatgaacacagagatattgcctgtgtgtttgcagagaagatggtttcta   1860

1861 taaagagtaggaaagctgaaattatagtagagtctcctttaaatgcacattgtgtggatg   1920

1921 gctctcaccatttcctaagagatacagtgtaaaaacgtgacagtaatactgattctagca   1980

1981 gaataaacatgtaccacatttgcaaaaaa                                   2010 pcKGCEA2:

1 gggtggatcctaggctcatctccatagggagaacacacatacagcagagaccatggga    59
                                                              MetGly 60 cccctctcagcccctccctgcactcagcacatcacctggaaggggctcctgctcacagca  119
     ProLeuSerAlaProProCysThrGlnHisIleThrTrpLysGlyLeuLeuLeuThrAla 120 tcacttttaaacttctggaacctgcccaccactgcccaagtaataattgaagcccagcca  179
     SerLeuLeuAsnPheTrpAsnLeuProThrThrAlaGlnValIleIleGluAlaGlnPro 180 cccaaagtttctgaggggaaggatgttcttctacttgtccacaatttgccccagaatctt  239
     ProLysValSerGluGlyLysAspValLeuLeuLeuValHisAsnLeuProGlnAsnLeu 240 actggctacatctggtacaaagggcaaatgacggacctctaccattacattacatcatat  299
     ThrGlyTyrIleTrpTyrLysGlyGlnMetThrAspLeuTyrHisTyrIleThrSerTyr 300 gtagtagacggtcaaattatatgggcctgcctacagtggacgagaaacagtatattcc    359
     ValValAspGlyGlnIleIleTyrGlyProAlaTyrSerGlyArgGluThrValTyrSer 360 aatgcatccctgctgatccagaatgtcacacaggaggatgcaggatcctacaccttacac  419
     AsnAlaSerLeuLeuIleGlnAsnValThrGlnGluAspAlaGlySerTyrThrLeuHis 420 atcataaagcgaggcgatgggactggaggagtaactggatatttcactgtcaccttatac  479
     IleIleLysArgGlyAspGlyThrGlyGlyValThrGlyTyrPheThrValThrLeuTyr 480 tcggagactcccaagcgctccatctccagcagcaacttaaaccccagggaggtcatggag  539
     SerGluThrProLysArgSerIleSerSerSerAsnLeuAsnProArgGluValMetGlu 540 gctgtgcgcttaatctgtgatcctgagactccggatgcaagctacctgtggttgctgaat  599
     AlaValArgLeuIleCysAspProGluThrProAspAlaSerTyrLeuTrpLeuLeuAsn 600 ggtcagaacctccctatgactcacaggttgcagctgtccaaaaccaacaggaccctctat  659
     GlyGlnAsnLeuProMetThrHisArgLeuGlnLeuSerLysThrAsnArgThrLeuTyr 660 ctatttggtgtcacaaagtatattgcagggccctatgaatgtgaaatacggaggggagtg  719
     LeuPheGlyValThrLysTyrIleAlaGlyProTyrGluCysGluIleArgArgGlyVal
```

```
                                  -continued
 720 agtgccagccgcagtgacccagtcaccctgaatctcctcccgaagctgcccatgccttac    779
     SerAlaSerArgSerAspProValThrLeuAsnLeuLeuProLysLeuProMetProTyr 780 atcaccatcaacaacttaaaccccagggagaagaaggatgtgttagccttcacctgtgaa    839
     IleThrIleAsnAsnLeuAsnProArgGluLysLysAspValLeuAlaPheThrCysGlu 840 cctaagagtcggaactacacctacatttggtggctaaatggtcagagcctcccggtcagt    899
     ProLysSerArgAsnTyrThrTyrIleTrpTrpLeuAsnGlyGlnSerLeuProValSer 900 ccgagggtaaagcgacccattgaaaacaggatactcattctacccagtgtcacgagaaat    959
     ProArgValLysArgProIleGluAsnArgIleLeuIleLeuProSerValThrArgAsn 960 gaaacaggaccctatcaatgtgaaatacgggaccgatatggtggcatccgcagtaaccca   1019
     GluThrGlyProTyrGlnCysGluIleArgAspArgTyrGlyGlyIleArgSerAsnPro 1020 gtcaccctgaatgtcctctatggtccagacctccccagaatttaccCttacttcacctat   1079
     ValThrLeuAsnValLeuTyrGlyProAspLeuProArgIleTyrProTyrPheThrTyr 1080 taccgttcaygagaaaacctcgacttgtcctgctttgcggactctaacccaccggcagag   1139
     TyrArgSerGlyGluAsnLeuAspLeuSerCysPheAlaAspSerAsnProProAlaGlu 1140 tattttttggacaattaatgggaagtttcagctatcaggacaaaagctctttatcccccaa   1199
     TyrPheTrpThrIleAsnGlyLysPheGlnLeuSerGlyGlnLysLeuPheIleProGln 1200 attactacaaatcatagcgggctctatycttgctctgttcgtaactcagccactggcaag   1259
     IleThrThrAsnHisSerGlyLeuTyrAlaCysSerValArgAsnSerAlaThrGlyLys 1260 gaaatctccaaatccatgatagtcaaagtctctggtccctgccatggaaaccagacagag   1319
     GluIleSerLysSerMetIleValLysValSerGlyProCysHisGlyAsnGlnThrGlu 1320 tctcattaatggctgccacaatagagacactgagaaaaagaacaggttgataccttcatg   1379
     SerHisEnd 1380 aaattcaagacaaagaagaaaaaggctcaatgttattggactaaataatcaaaaggataa   1439

1440 tgttttcataattttttattggaaaatgtgctgattcttggaatgttttattctccagatt   1499

1500 tatgaactttttttcttcagcaattggtaaagtatactttttgtaaacaaaaattgaaaca   1559

1560 tttgcttttgctctctatctgagtgccccccc                                1591 .
```

It will be appreciated that the instant specification and claims are set forth by way of illustration and not limitation and that various modifications and changes may be made without departing from the spirit and scope of the present invention.

What is claimed is:

1. A polypeptide expressed by a cell that is transfected, infected or injected with a recombinant cloning vehicle, said recombinant cloning vehicle coding for a CEA family polypeptide selected from the group consisting of sequences TM-2, TM-3, KGCEA1 and KGCEA2, or a labeled form of said polypeptide.

2. A peptide having an amino acid sequence corresponding to the entire amino acid sequence or a fragment thereof of the expression product of a cell that is transfected, infected or injected with a recombinant cloning vehicle, said fragment exhibiting immunological cross-reactivity with a CEA family member and having no less than five amino acids, and said recombinant cloning vehicle coding for a CEA family polypeptide selected from the group consisting of sequences TM-2, TM-3 KGCEA1 and KGCEA2, or a synthetic peptide corresponding to said expression product, or a labeled form thereof.

* * * * *